United States Patent [19]

Curchod

[11] Patent Number: 5,791,351
[45] Date of Patent: Aug. 11, 1998

[54] MOTION MEASUREMENT APPARATUS

[76] Inventor: Donald B. Curchod, 1023 Los Trancos Rd., Portola Valley, Calif. 94028

[21] Appl. No.: 692,107

[22] Filed: Aug. 5, 1996

Related U.S. Application Data

[63] Continuation of Ser. No. 250,152, May 26, 1994.

[51] Int. Cl.[6] ............................................. A61B 5/117
[52] U.S. Cl. .................................. 128/782; 128/774
[58] Field of Search ..................... 439/252; 128/774, 128/782; 33/511, 512

[56] References Cited

U.S. PATENT DOCUMENTS

| | | | |
|---|---|---|---|
| 4,582,325 | 4/1986 | Yuhara | 128/782 |
| 4,665,928 | 5/1987 | Linial et al. | 128/782 |
| 4,839,809 | 6/1989 | Leighton et al. | 128/728 X |

OTHER PUBLICATIONS

Article entitled "Computer Aided Swing", Popular Mechanics, Jun. 1992, p. 42, Jun. 1992.

*Primary Examiner*—Sam Rimell
*Attorney, Agent, or Firm*—James J. Leary

[57] ABSTRACT

This invention is an apparatus for measuring and visually displaying a user's body movement while performing a motion. Sensing means (22) such as potentiometers, are coupled to the joints of a user in order to quantitatively detect movement of the user's body while performing a motion. The sensors (22) generate signals indicative of the motion and are received by processor means (30) which in turn connects to a display means (32) for graphically displaying at least one image representing the movement. A second image may be displayed with the first image for comparison purposes.

23 Claims, 20 Drawing Sheets

000
MOTION MEASUREMENT APPARATUS

This is a continuation of application Ser. No. 08/250,152 filed May 26, 1994.

BACKGROUND OF THE INVENTION

1. Field of the Invention.

The present claimed invention relates to movement of the human body. Specifically, the present claimed invention relates to measuring movements of the human body which occur while performing a motion.

2. Prior Art.

Monitoring and quantitatively measuring the movement of the human body while performing a motion is essential in many fields such as, for example, sports instruction or physical therapy. However, many of the motions of interest are performed very quickly and make observation and analysis difficult or impossible. furthermore, most prior art teachings or instruction techniques are performed by observing or recording the motion of a performer and then the performer's body movement. That is the performer's body movement is not analyzed or reviewed during the performance of the motion, but is instead delayed until after the performer has completed the motion. As a result, it is often difficult to alter or correct aspects of the performer's body movement using prior art teaching or instruction techniques.

Additionally, many prior art systems for monitoring the movement of a human body employ complicated and costly detection systems. For example, prior art motion monitoring systems commonly generate optical or acoustic signals which are directed towards the performer. Detectors then receive signals reflected from the performer and use the reflected signals to analyze movement of the user's body. However, such systems are bulky, often taking up an entire room or even larger areas. In addition to their considerable bulk, such prior art systems are also extremely expensive. Thus, many of the prior art systems for monitoring the movement of a human body are not well suited for personal private use. That is, the considerable cost, bulk, and complexity associated with prior art systems prohibits their use for most consumers.

Thus, the need has arisen for a compact, inexpensive system to monitor the movement of a human body while performing a motion, which does not require the complex detection systems found in the prior art, and which provides for approximate real time observation of the body movement of a performer while performing a motion.

SUMMARY OF THE INVENTION

It is therefore an object of the present invention to provide a compact, inexpensive system to monitor the movement of a human body while performing a motion, which does not require the complex detection systems found in the prior art, and which provides for approximate real time observation of the body movement of a performer while performing a motion. The above object has been achieved by a compact structure wherein sensors are coupled to a user's body at joints of the user's body which are moved while a user performs a motion. The user's body movement, as quantitatively measured by the sensors, is graphically displayed on a display screen at approximately the same time the user performs the motion. Thus, by placing the display screen within view, the user is able to observe his or her body movements in real time, that is while he or she performs the motion. In so doing, the user is able to correct or alter body movements in order to more correctly perform the motion.

In another embodiment, the user's body movement, as quantitatively measured by the sensors, is graphically displayed on a display screen concurrently with a second image. The second image can represent a prior performance of the motion by the user, or can represent a performance of the motion by a second user, such as for example, a professional who performs the motion in an "ideal" manner. In so doing, not only is the user able to observe his or her body movements in real time, but the user is also able to compare those body movements to the ideal body movements of a professional, and adjust his or her own movements to match that ideal standard.

In still another embodiment, two different images representing separate prior performances of the motion by the user can be simultaneously displayed and compared on the display screen. In so doing, the user is able to see, for example, improvements of changes in his body movements when performing the motion. In still another embodiment, a technique for one, two or three dimensional head tracking is provided. This technique has minimal encumbrance and reduces head movement limitation and provides a more comfortable, easy to use, easy to wear and easy to take off head tracking system. The system could work in all or just one of the X, Y, Z coordinates. The invention uses a harness shaped to conform to the shoulders of a user. The shoulder harness is supported on the shoulder in a stable, secure manner by virtue of its own weight and does not require to be fastened or strapped to the body of user.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims.

Figure 1:
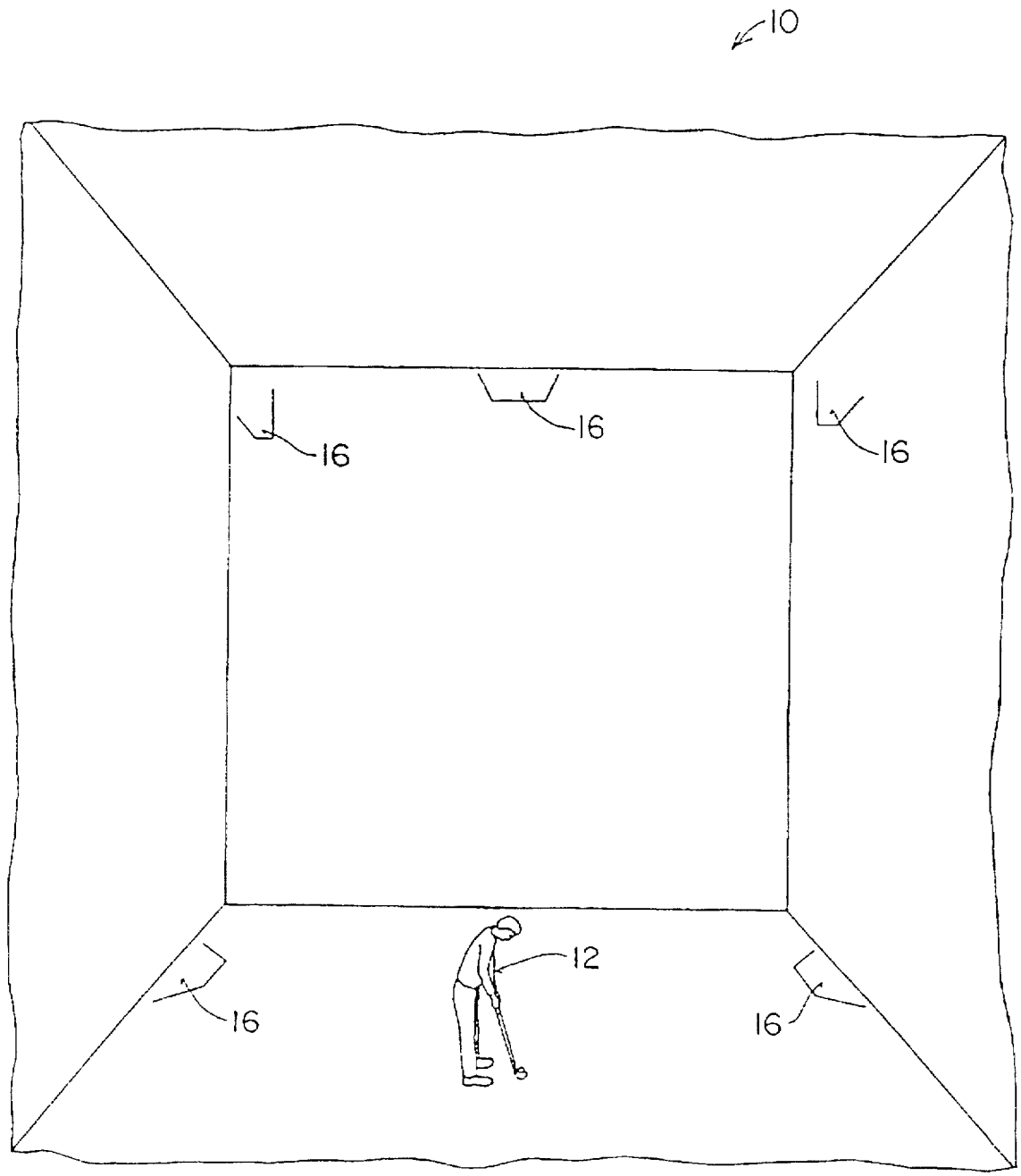
FIG. 1 is a perspective view of a prior art motion detector.

With reference now to Prior Art FIG. 1, a prior art motion detector 10 is shown. Prior art motion detector 10 is employed in Prior Art FIG. 1 to measure the body movements of a golfer 12 while golfer 12 performs a golf swing. As shown in Prior Art FIG. 1, prior art motion detector 10 occupies an entire room 14, and requires the use of several signal generators and detectors 16. Additionally, golfer 12 is only able to view his body movements after he has performed the golf swing and his body movements have been recorded.

Figure 2:
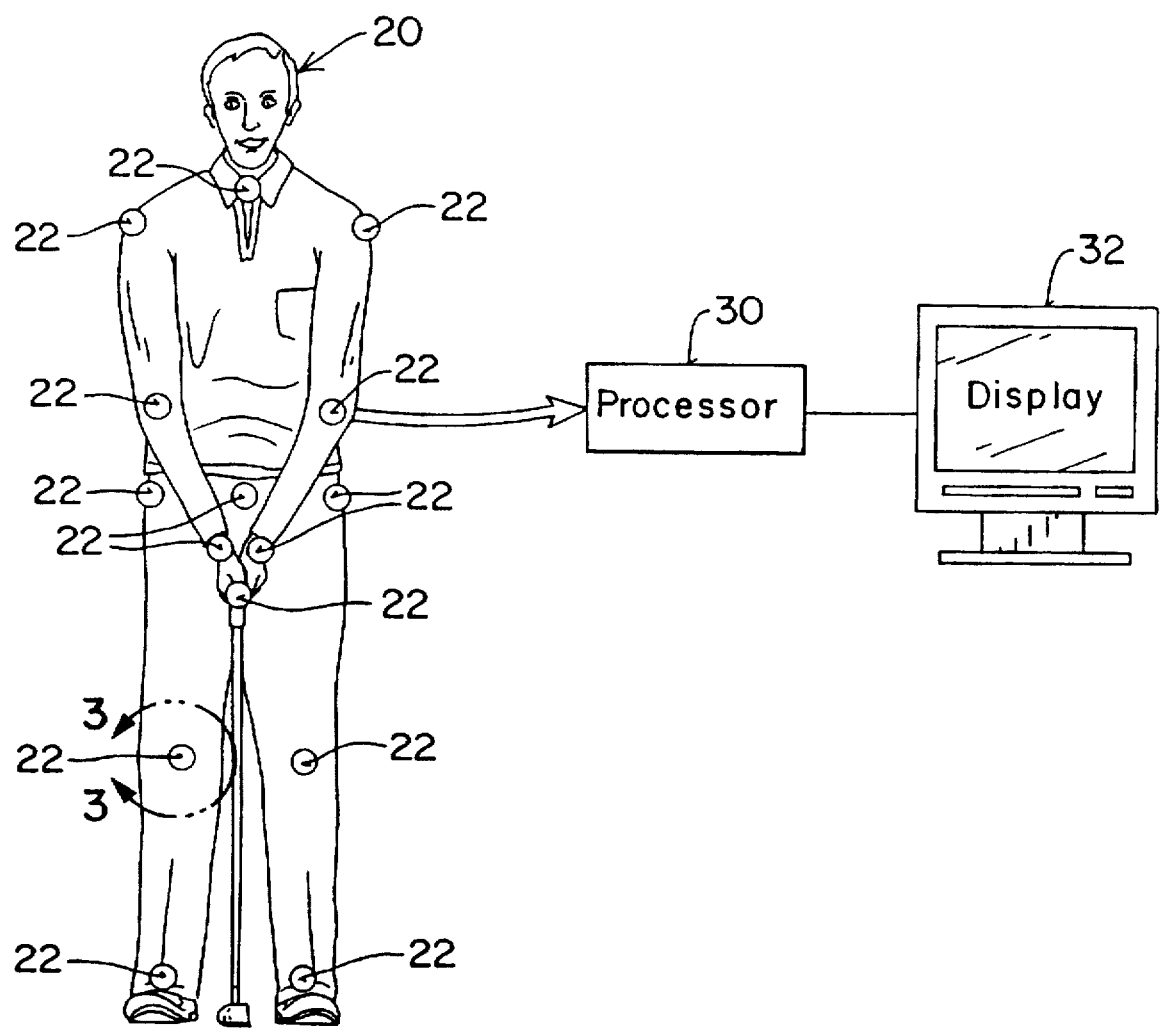
FIG. 2 is a perspective view of a golfer using a motion measurement apparatus constructed in accordance with the present claimed invention.

With reference now to FIG. 2, a motion measurement apparatus constructed in accordance with an embodiment of the present claimed invention for measuring body movements which occur when performing a golf swing is illustrated. Although the present embodiment specifically relates to an apparatus for measuring body movements which occur while performing a golf swing, the present claimed invention is also well suited to measuring body movements which occur while performing various other motions, such as, for example, a tennis stroke, other sports related motions, or dance movements. In addition, the present motion measurement invention is also well suited to incorporating the user's body motion into, for example, a video arcade game, or for converting the various movements of the user's body to corresponding musical tones.

With reference still to FIG. 2, a golfer 20 has inexpensive and compact sensors 22 attached to his body at joints which are moved while golfer 20 performs a golf swing. Sensors 22 are attached to the joints of golfer 20 such that sensors 22 quantitatively measure the movement of the joints of golfer 20 while golfer 20 performs the golf swing. Sensors 22 are attached to joints of golfer 20 in such a manner that sensors 22 do not interfere with the movement of the joints while golfer 20 performs a golf swing.

Figure 3:
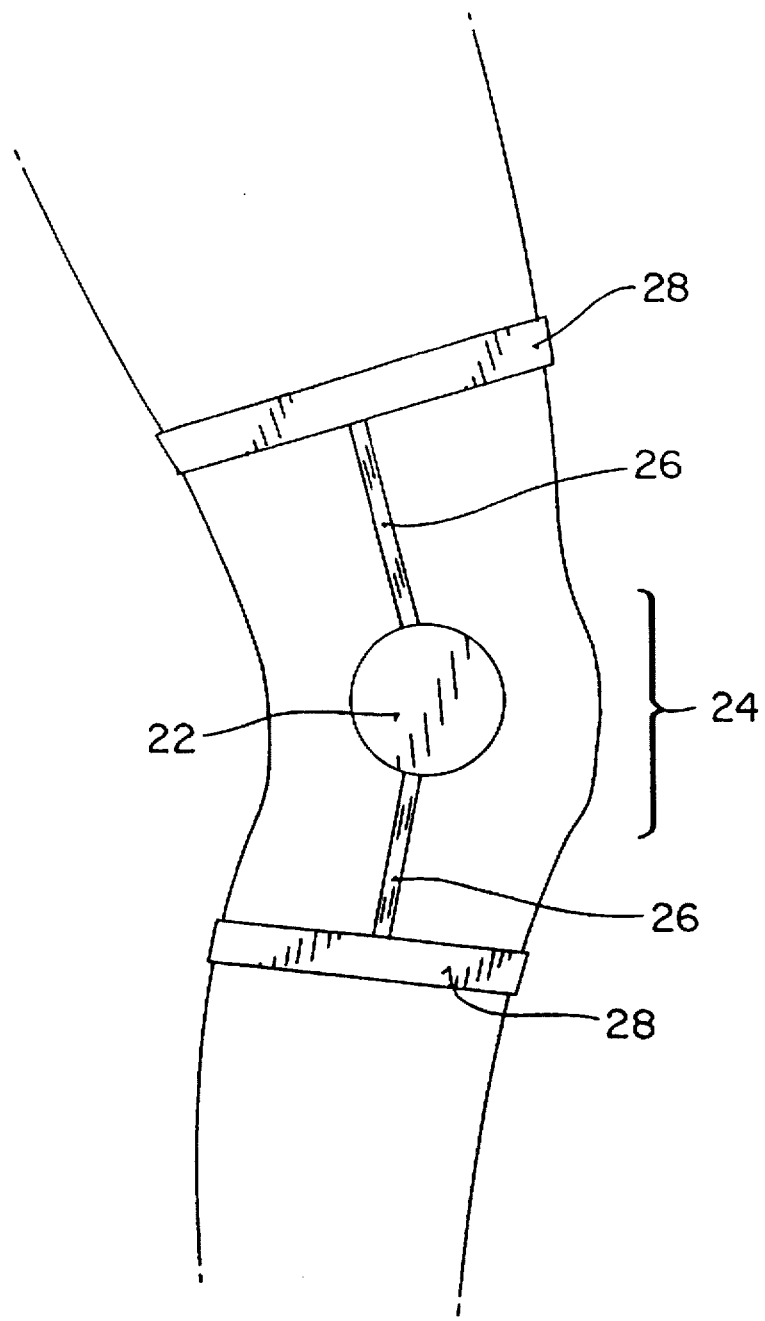
FIG. 3 is a side view of a knee joint of a golfer having a sensor attached thereto in accordance with the present claimed invention.

With reference next to FIG. 3, an enlarged view of an example of a knee joint 24 of golfer 20 of FIG. 2 having a sensor 22 attached thereto is shown. As shown in FIG. 3, sensor 22 is attached to knee joint 24 in a manner such that knee joint 24 is able to move without interference from sensor 22. In the present embodiment, rods 26 extending from sensor 22 are fastened above and below knee joint 24 using straps 28. As knee joint 24 straightens or bends, sensor 22 detects the movement of rods 26 and generates an electric signal indicative of the shift in position of knee joint 24. In so doing, quantitative measurement of the movement of knee joint 24 and all other joints to which sensors 22 are attached is achieved. Although, potentiometers are used as sensors 22 in the present embodiment, the present claimed invention is also well suited to the use of numerous other types of sensors well known in the art such as, for example, stepper motors, optical sensors, or magnetic sensors.

With reference still to FIG. 3, sensors 22 quantitatively measure the movement of joints in more than one dimension where needed. That is, a sensor 22 located at, for example, the elbow of golfer 20 of FIG. 2 measures both the amount of bending of the elbow and also the amount of rotation which occurs between the elbow and the wrist as golfer 20 performs a golf swing. In so doing, all of the critical body movements of golfer 20 which occur during the performance of a golf swing can be quantitatively measured by sensors 22.

Figure 4:
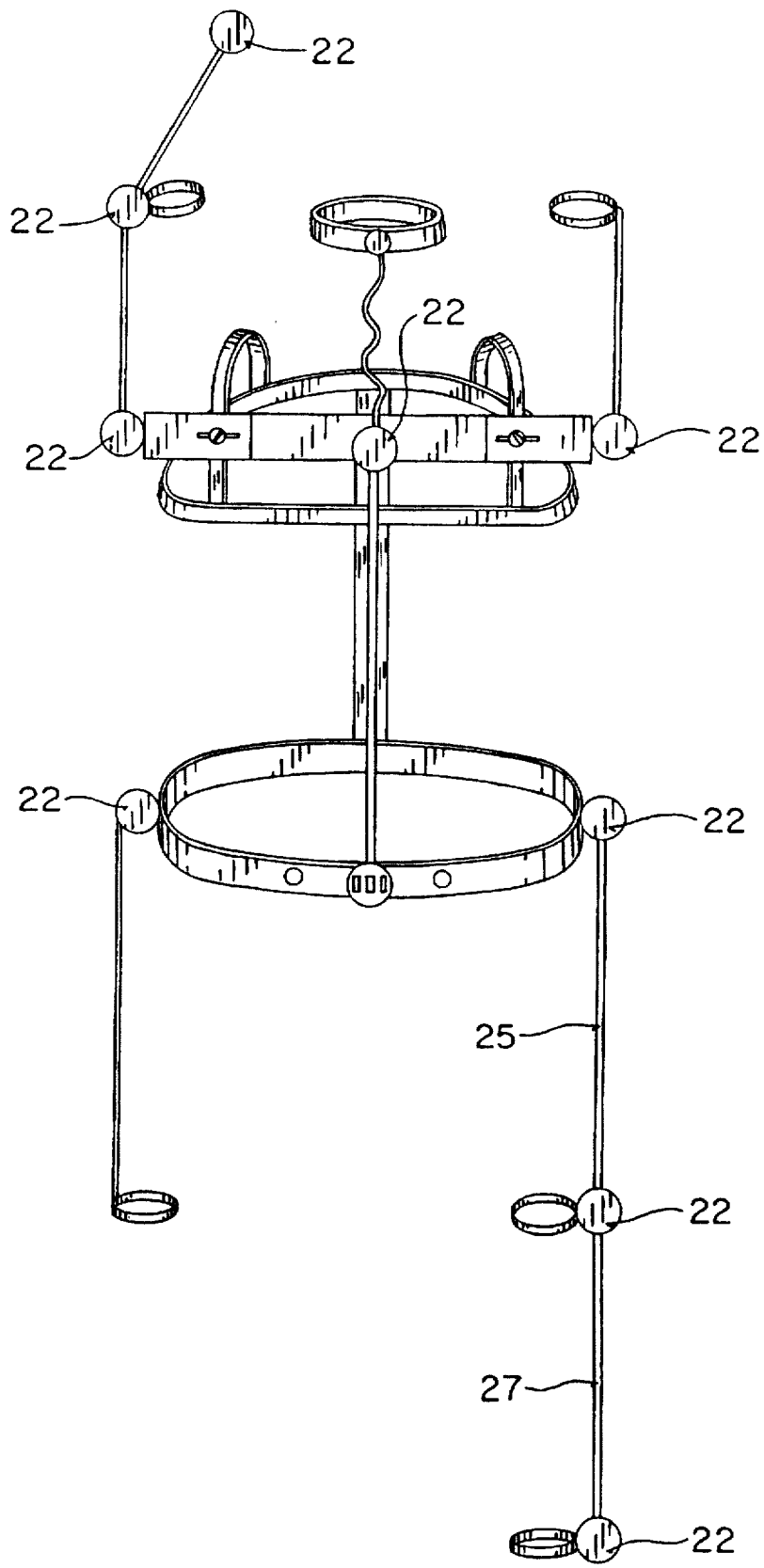
FIG. 4 is a perspective view of another embodiment of the present invention in which adjacent sensors are interconnected to form a single structure in accordance with the present claimed invention.

With reference next to FIG. 4, another embodiment of the present claimed invention is shown in which adjacent sensors 22 are interconnected using, for example, metal tubing. That is, in the present embodiment, instead of having rods 26 of FIG. 2 strapped to the leg of golfer 20 of FIG. 2, rods 26 would extend and be attached to adjacent sensors. As shown in FIG. 4, a tube 25 connects sensors 22 located at the hip and at the knee of golfer 20. Another tube 27 connects sensors 22 located at the ankle and knee of golfer 20. As a result, a single structure is formed wherein sensors 22 function as joints between connected tubes. By forming a single structure as set forth in the present embodiment, golfer 20 of With reference again to FIG. 2, a processor 30 receives and processes signals generated by each of sensors 22. The processed signals are then transmitted to a display unit 32. Display unit 32 then displays an image such as, for example, a stick figure which duplicates the body movements of golfer 20 as golfer 20 performs a golf swing. That is, display unit 32 displays in approximately real time, an image which represents the body movements of golfer 20 as golfer 20 performs a golf swing. Therefore, by placing display unit 32 within view of golfer 20, golfer 20 is able to observe his body movements, as depicted by an image on display unit 32, while golfer 20 performs a golf swing. In so doing, golfer 20 can immediately alter or correct his body positioning and/or body movements until he generates an image on display unit 32 which exhibits desired body position and/or body movements. Additionally, although processor 30 of FIG. 2 is shown located next to the body of golfer 20, processor 30 may also be contained within a small housing, not shown, and attached to the body of golfer 20 in a convenient location such as, for example, the back of golfer 20.

Figure 5A:
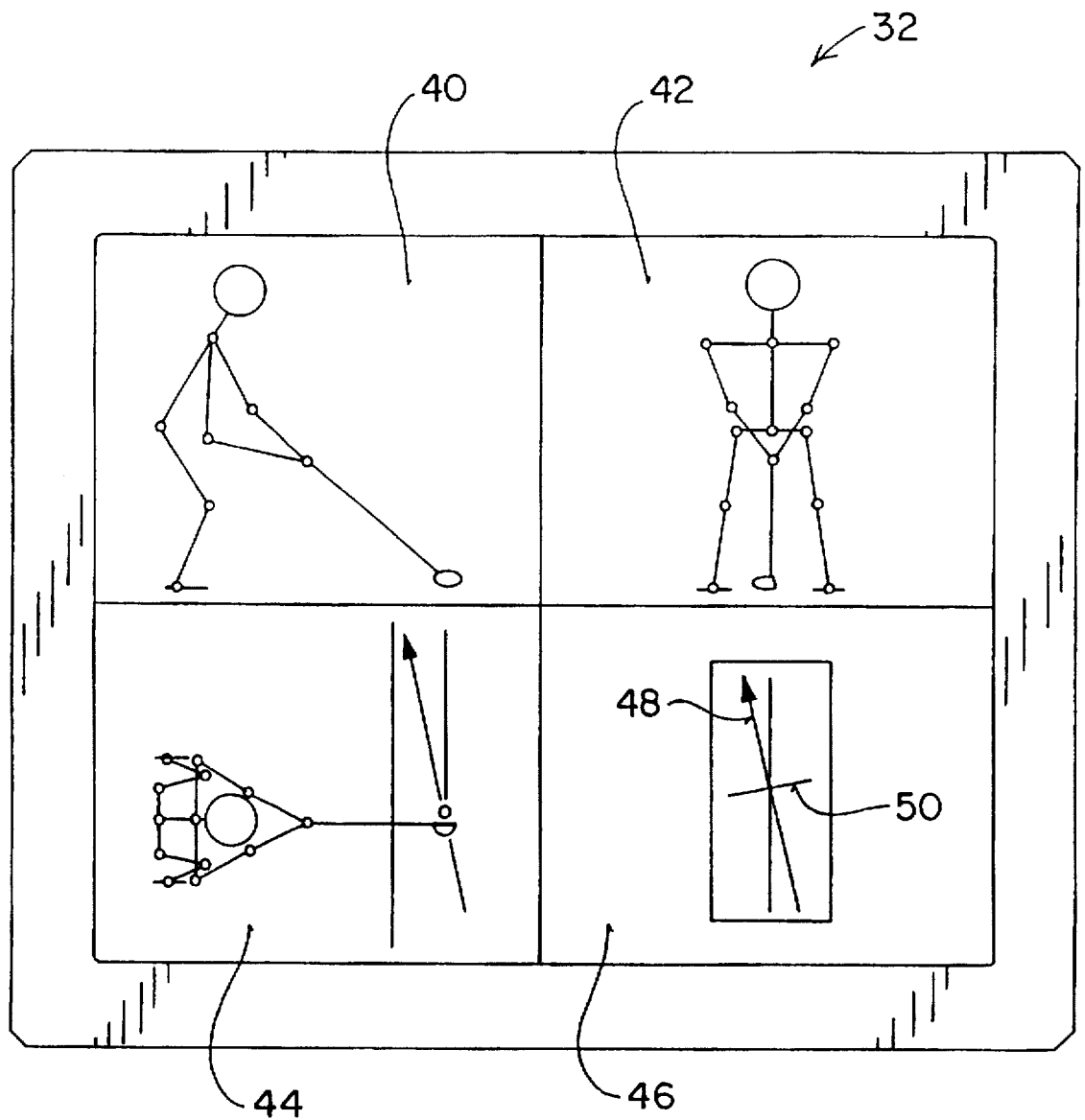
FIG. 5A shows a series of images duplicating the body movements of a golfer which can be displayed on a display unit while the golfer performs a golf swing in accordance with the present claimed invention.

With reference next to FIG. 5A, an example of a series of typical images which can be displayed together as a group or individually on display unit 32 are shown. In the present embodiment, image 40 representing a side view of golfer 20 of FIG. 2 is displayed on display unit 32. In operation, as golfer 20 prepares to use the present invention, golfer 20 would attach sensors 22 of FIGS. 2–4 to his body and then calibrate sensors 22 and processor 30 according to the golfer's individual size and dimensions. In the present embodiment, this calibration process only needs to be performed once. Next, golfer 20 would address the golf ball and observe the body position of image 40 on display unit 32. In so doing, golfer 20 would be able to observe any obvious flaws or improper body positioning occurring while golfer 20 addresses a golf ball. As a result, golfer 20 is able to quickly "self-correct" his golf stance and alter his body positioning until image 40 is arranged in the proper or desired position. Likewise, as golfer 20 performs a golf swing, golfer 20 is able to observe image 40 on display unit 32 at each moment during the golf swing and immediately recognize and correct any imperfections in his body position or his body movements. That is, the present claimed invention provides for approximate real time observation of the body movement and positioning of a golfer while the golfer is performing a golf swing. Thus, golfer 20 is able to receive immediate feedback and is better able to identify mistakes or imperfections in his golf swing.

With reference again to FIG. 5A, although the present embodiment provides for approximate real time observation of an image representing golfer 20, the present claimed invention is also well suited for storing the image representing the body movement and positioning of golfer 20 and displaying the image at a later time. By storing the image, golfer 20 of FIG. 2 can either view the image immediately after performing the swing or wait until a later more convenient time.

With reference still to FIG. 5A, in another embodiment of the present invention multiple images such as, for example, images 40, 42, and 44 of golfer 20 are displayed at the same time on display unit 32. Images 40, 42, and 44 show the body position and movement of golfer 20 from several different angles. Line 48 of image 46 depicts the path of the head of the golf club just prior to and after the golf club contacts a golf ball. Thus, golfer 20 is able to observe his body position and movements in real time from several different angles, and golfer 20 is able to observe the path of the club head as it strikes a golf ball. Although the present embodiment, employs images such as images 40, 42, 44, and 46, the present claimed invention is also well suited to numerous other types of images which can be graphically displayed on display unit 32. Furthermore, the present claimed invention is also well suited to displaying information such as club head speed, distance that a golf ball would be hit, or other relevant information on display unit 32.

Figure 5B:
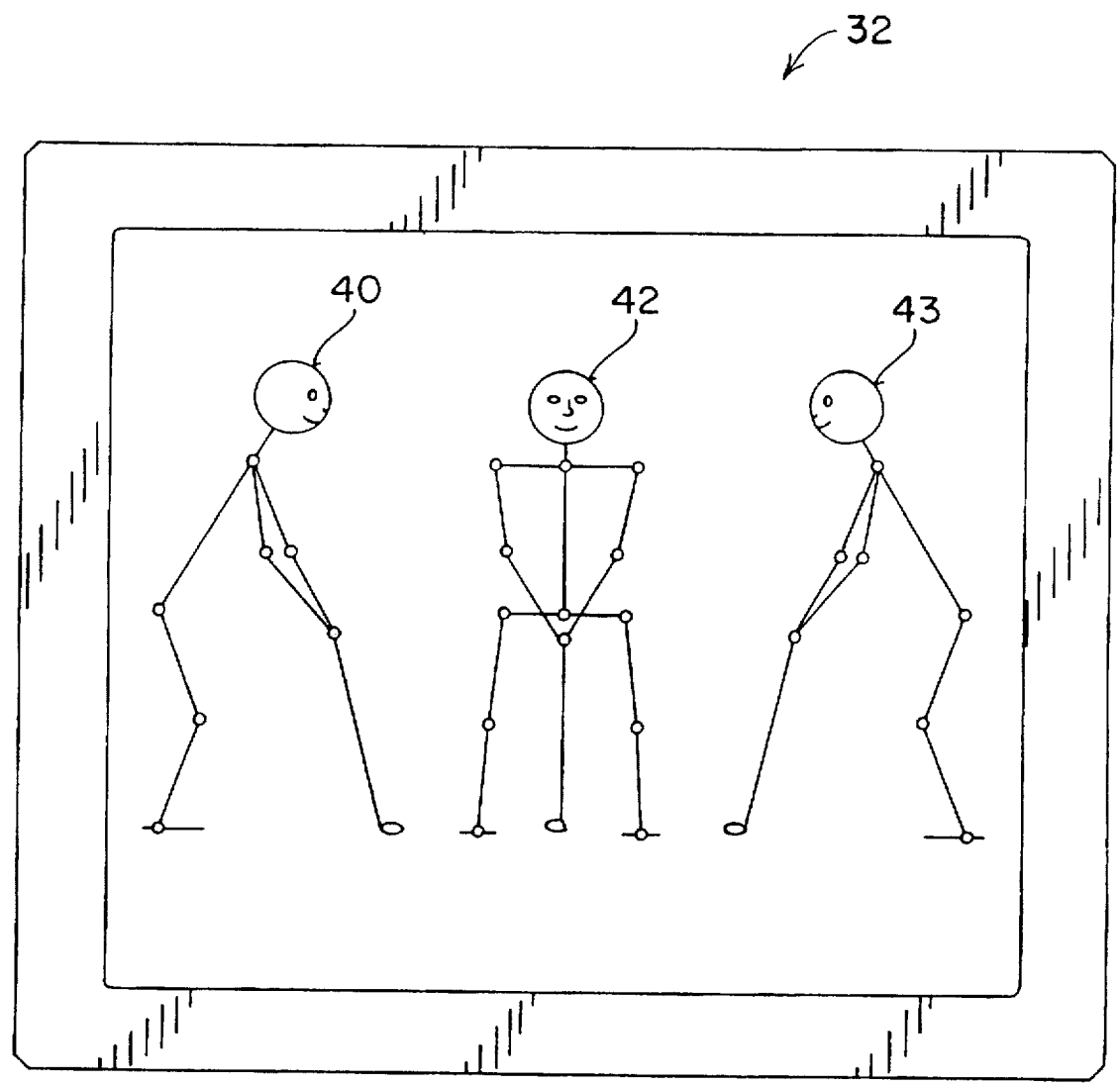
FIG. 5B shows a series of images duplicating the body movements of a golfer displayed wherein the images are arranged side-by-side on a display unit while the golfer performs a golf swing in accordance with the present claimed invention.

With reference next to FIG. 5B, the present invention is also well suited to displaying several images of the body position of golfer 20, wherein each of the images represents a different view of the body of golfer 20. As shown in FIG. 5B, a right side view 40, a front view 42, and a left side view 43 may be displayed, for example, side-by-side. Although such views are shown in FIG. 5B, the present invention is also well suited to displaying other views, and placing those views in different arrangements on display unit 32.

Figure 6A:
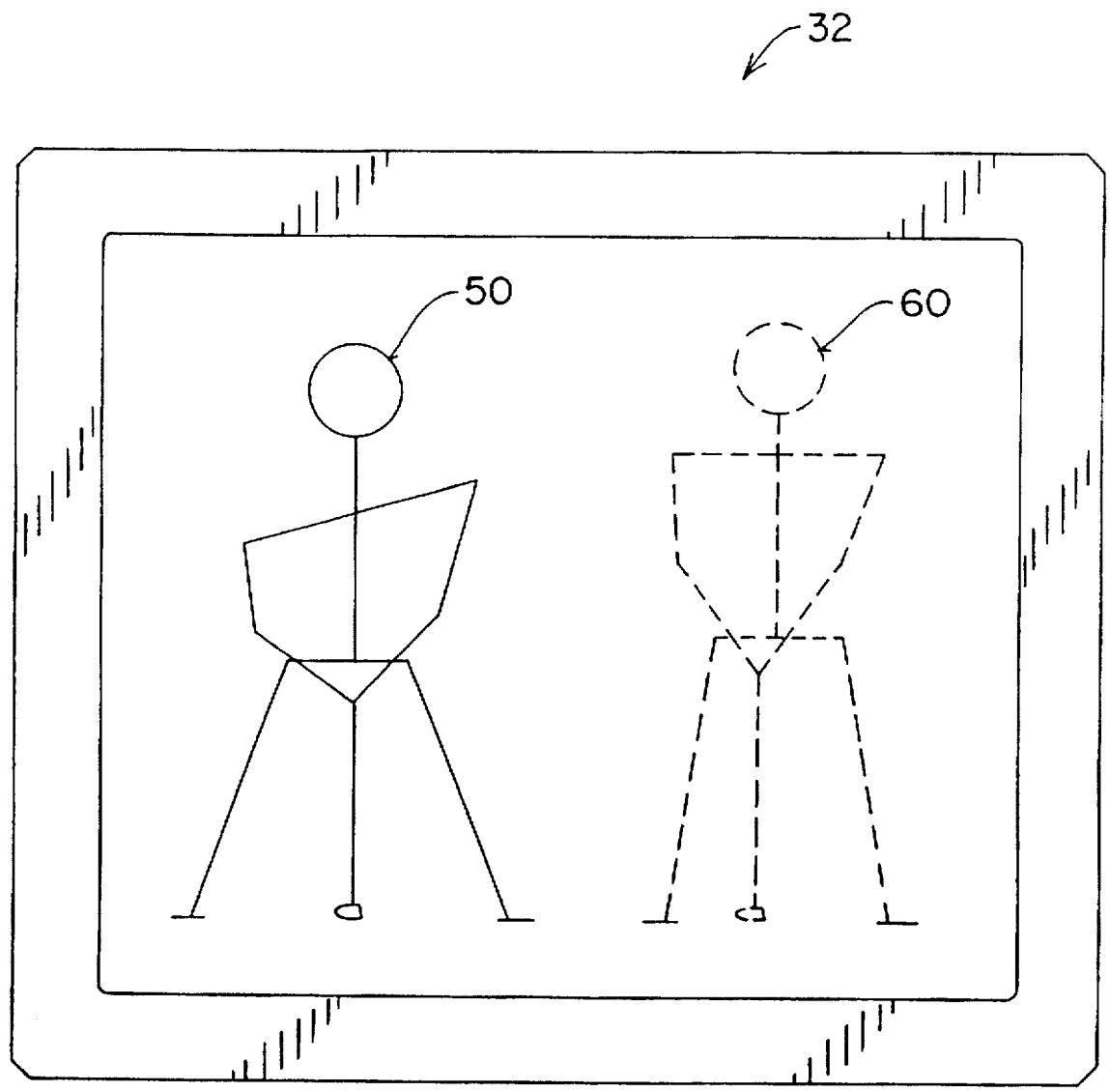
FIG. 6A shows another embodiment of the present claimed invention in which two images having differing body positioning are displayed concurrently on a display unit in accordance with the present claimed invention.

With reference next to FIG. 6A, yet another embodiment of the present claimed invention is shown in which two images 50 and 60 are displayed concurrently on display unit 32. In the present embodiment, image 50 represents the body position and body movements of golfer 20 of FIG. 2. Dotted image 60 represents a "sample" golfer whose body position and movements are stored in the memory of processor 30. Image 60 represents, for example, a stored record of the best previous golf swing of golfer 20, a golf swing of the instructor of golfer 20, a golf swing of a professional golfer, or a computer generated golf swing. Therefore, the present invention allows for real time observation by golfer 20 of his own golf swing, and also allows for real time comparison by golfer 20 of his golf swing with an "ideal" golf swing. Thus, golfer 20 is able to immediately alter his body position and movements during his golf swing so that his movements duplicate the body position and body movements of an ideal golfer. Although image 60 is dotted in the present embodiment, the present invention is also well suited to numerous types of image displays to differentiate image 50 from image 60, such as, for example, using different colors for images 50 and 60.

Figure 6B:
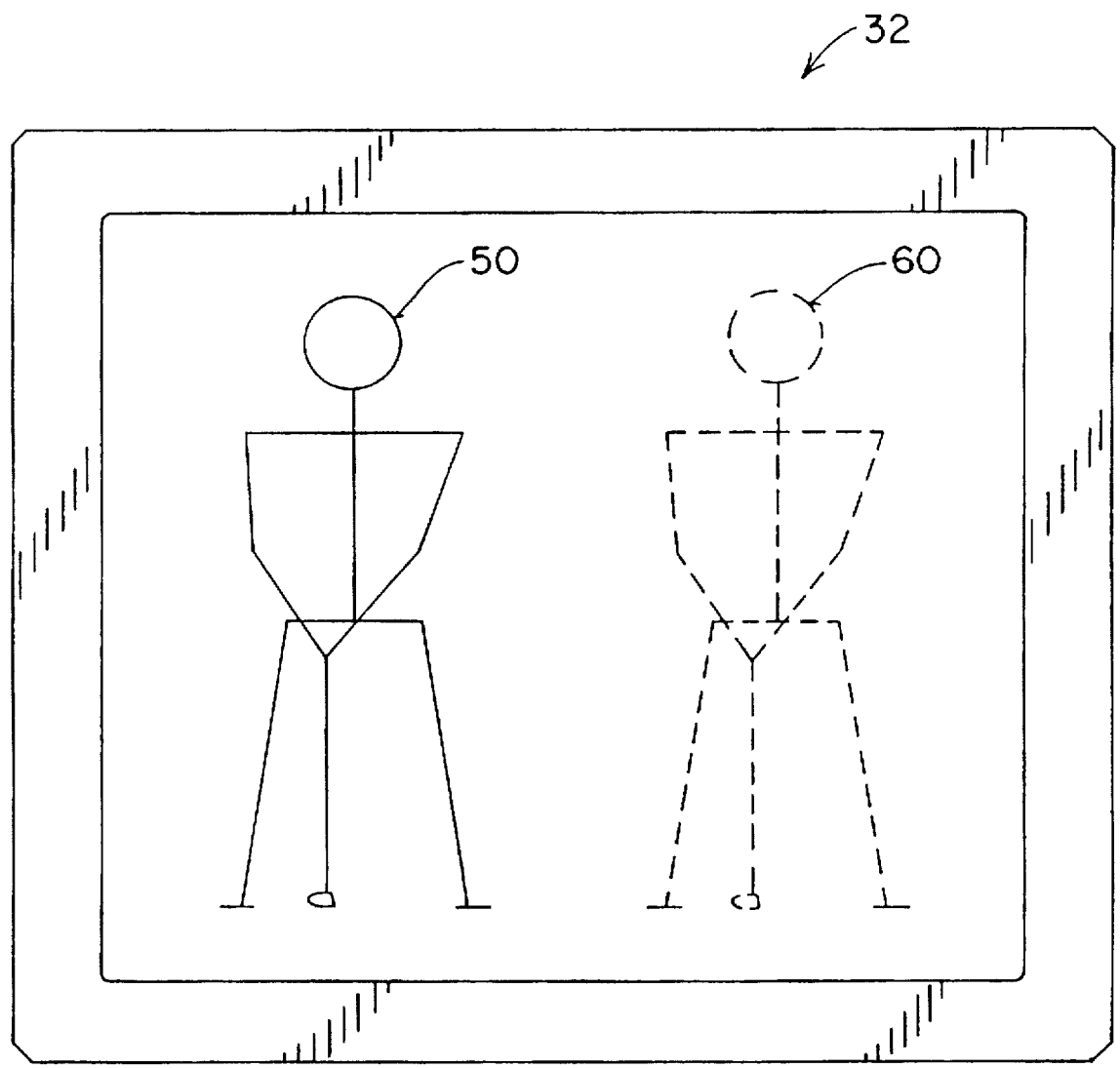
FIG. 6B shows the images of FIG. 6A in which the two images have the same body positioning and are displayed concurrently on a display unit in accordance with the present claimed invention.

With reference again to FIG. 6A, if image 60 represents an ideal golf stance, golfer 20 of FIG. 2 would immediately be able to realize that his right shoulder is dipped too low, and that his legs are spread too far apart. Golfer 20 would then alter his stance and body position until image 50 matches image 60 as shown in FIG. 6B.

With reference again to FIG. 6A, in the present embodiment, the hands of image 50 are used as a common reference point with image 60. For example, if golfer 20 is in the act of a back swing and has raised his hands to his waist such that the hands of image 50 are at waist level, the hands of image 60 will also be at waist level. The rest of image 60 will then be located at the ideal position for a golfer whose hands are at waist level during a back swing. By sharing a common reference point, golfer 20 is always able to observe the position in which his body should be arranged at every point along his golf swing. That is, when the hands of golfer 20 are at shoulder level during a follow through, the hands of image 60 will also be at shoulder level, and golfer 20 is able to immediately determine how the rest of his body should be positioned when his hands are at shoulder level during a follow through. Although the hands are used as a common reference point in the present embodiment, the present invention is also well suited to using other portions of the golfer's body as a common reference point with image 60.

With reference still to FIG. 6A, as an additional benefit of the present invention, golfer 20 of FIG. 2 can also select to have image 60 perform the ideal golf swing at several different speeds. Specifically, image 60 can perform the golf swing at a much slower rate than normal in order to allow golfer 20 time to adjust his body position and movements accordingly. However, the present invention is also well suited to having image 60 perform the golf swing at the same speed as which the sample golfer would perform the golf swing. In so doing, the present invention makes it possible for golfer 20 to observe in real time the proper tempo of an ideal golf swing. For example, if image 50 of golfer 20 has finished his swing before image 60 has completed his swing, golfer 20 knows that he must slow his swing in order to achieve an ideal tempo. Thus, the present invention not only provides for real time observation of body position and body movements during a golf swing, but also provides for real time observation of the tempo of a golf swing.

Figure 6C:
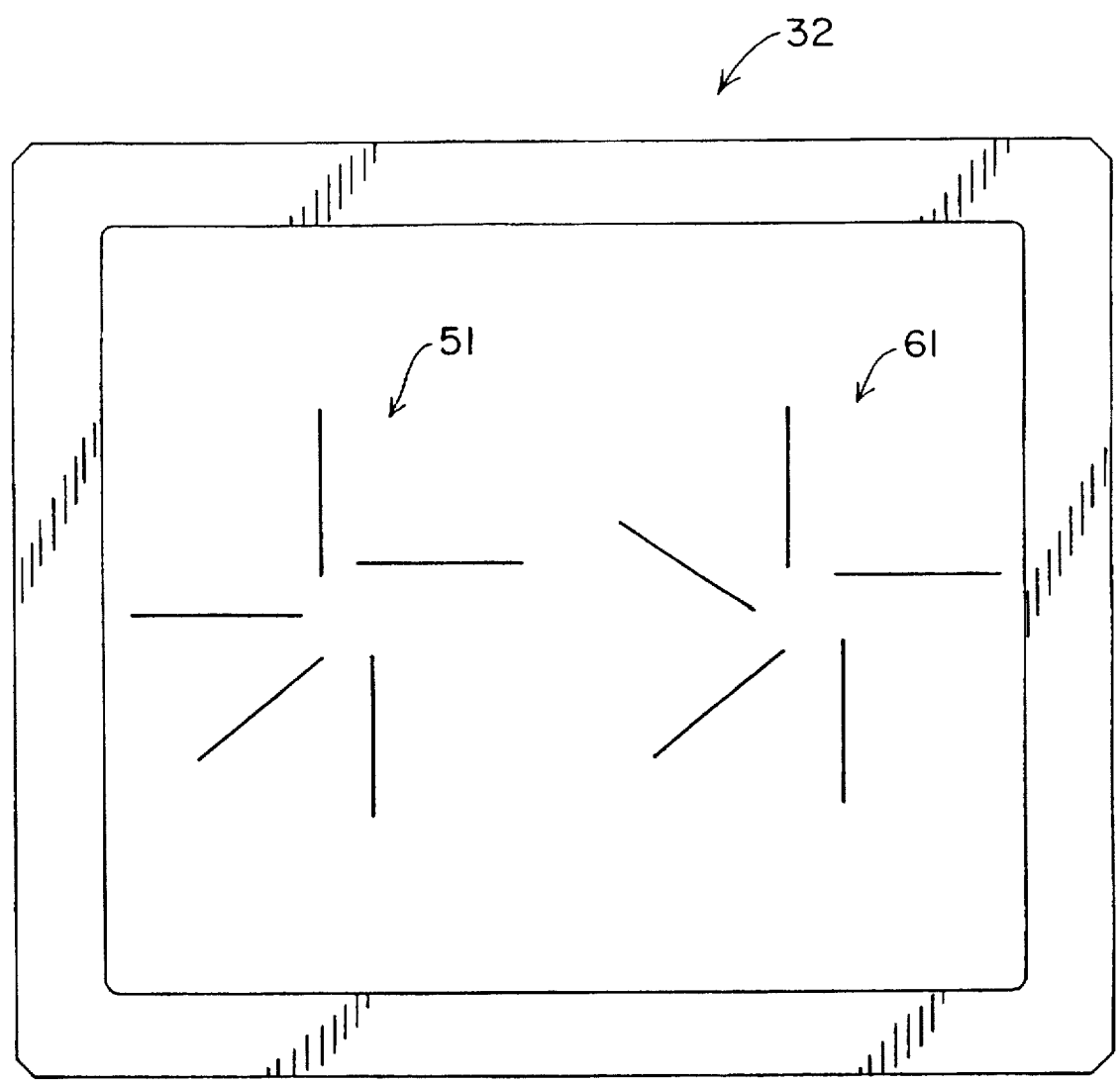
FIG. 6C shows a "fan" type display of the position of the golf club of a golfer and the position of the golf club of a sample golfer at different times during a golf swing in accordance with the present claimed invention.

Referring next to FIG. 6C, another embodiment of the present invention is shown in which "fan" type displays of the position 51 of the golf club of golfer 20 of FIG. 2 and the position 61 of the golf club of a sample golfer at different times during a golf swing is shown. By displaying the position of the golf club at different times, golfer 20 is able to observe how the position 51 of his golf club differs from that of the ideal sample golfer. Thus, golfer 20 can observe in real time the difference in speed and tempo between his golf swing and an ideal golf swing. Although only the position of the golf club is shown in FIG. 6C, the present claimed invention is also well suited to displaying a fan type image showing the entire body or any portion thereof of golfer 20.

Figure 7:
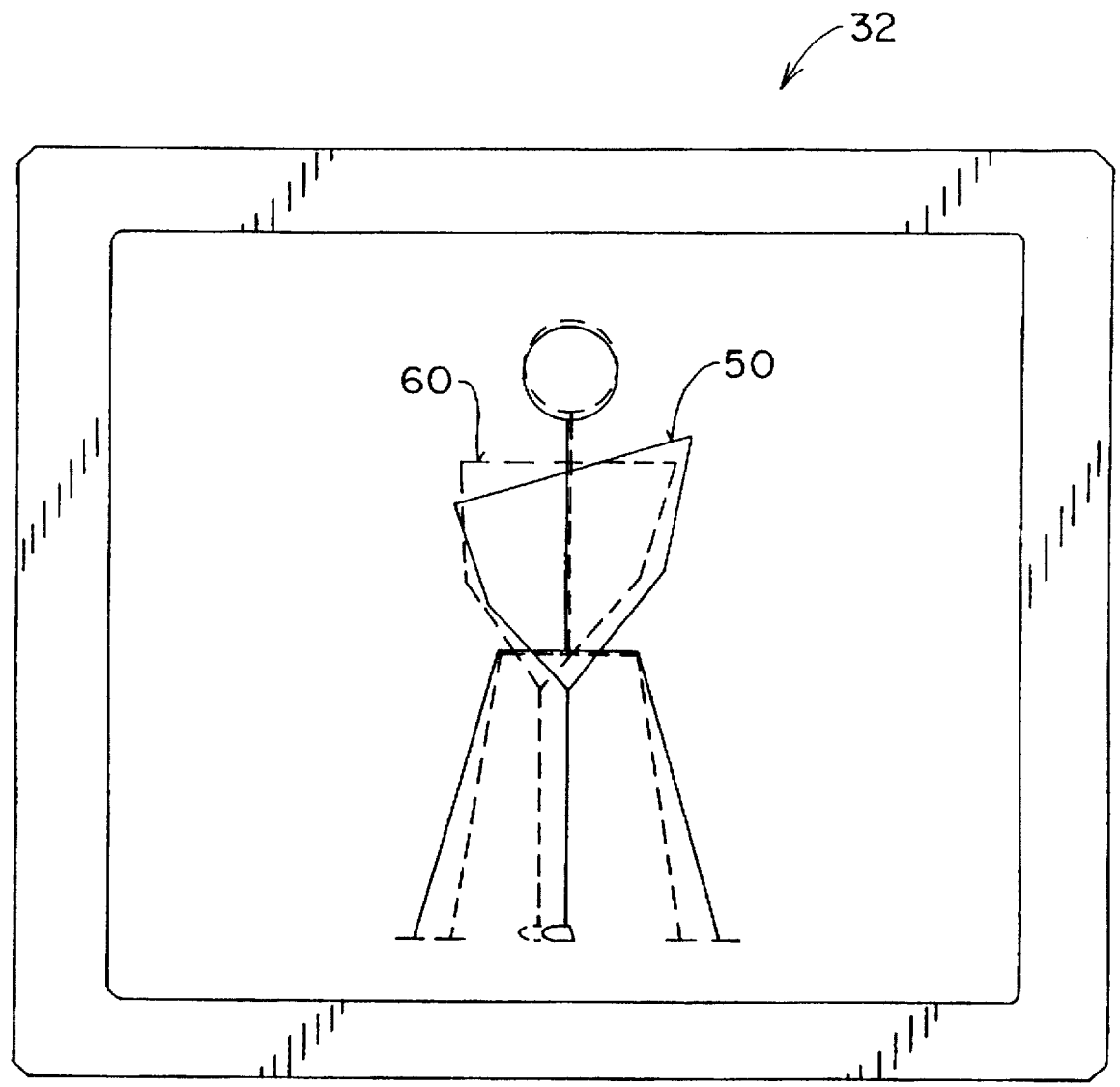
FIG. 7 shows another embodiment of the present claimed invention in which two images are displayed concurrently and overly each other on a display unit in accordance with the present claimed invention.

With reference next to FIG. 7, another embodiment of the present invention is shown in which two images 50 and 60 are displayed concurrently and overly each other on display unit 32. As in FIGS. 6A and 6B, image 50 represents the body position and body movements of golfer 20 of FIG. 2. Image 60 again represents, for example, a stored record of the best previous golf swing of golfer 20, a golf swing of the instructor of golfer 20, or a golf swing of a professional golfer whose body position and movements are stored in the memory of processor 30. By overlying the images as set forth in the present embodiment, golfer 20 can easily determine differences between his body position as represented by image 50 and the ideal body position as represented by image 60.

With reference again to FIG. 7, in the present embodiment, in order to further highlight the differences between image 50 and image 60, visual cues are indicated on display unit 32. These visual cues include, for example, "flashing" the portions of image 50 which are positioned differently than ideal image 60. That is, the shoulders and legs of image 50 would flash to indicate to golfer 20 of FIG. 2 that his right shoulder is dipped too low and that his legs are spread too far apart. The flashing in the present embodiment may also be controlled such that the flashing would, for example, be more rapid the farther the improperly positioned portions of image 50 were from the desired position. By displaying these visual cues, the present claimed invention assists golfer 20 in realizing errors in his body position and his body movements during the performance of a golf swing. Although flashing is used as the visual cue in the present embodiment, the present invention is also well suited to various other types of visual cues such, for example color changes, or changes in the intensity of portions of image 50. When color changes are used as the visual cue, the color of image 50 would be, for example, green when image 50 matches ideal image 60, yellow when image 50 differs slightly from the positioning of image 60, and red when image 50 greatly differs from image 60.

With reference still to FIG. 7, the present invention also allows golfer 20 of FIG. 2 to adjust the sensitivity of the visual cues. That is, golfer 20 is able to program processor 30 of FIG. 2 to only generate a visual cue such as, for example, flashing when the positioning of any portion of image 50 varies greatly from the positioning of image 60. In so doing, if golfer 20 is a beginner, he can decrease the sensitivity of the visual cues so that he is not alerted to minute differences between image 50 and image 60. However, as the skill of golfer 20 improves, he can heighten the sensitivity of the visual cues so that he is alerted to even minor differences between the positioning of image 50 and image 60. Thus, as golfer 20 improves he can "fine tune" his golf swing to almost completely match the ideal golf swing represented by image 60.

With reference again to FIG. 7, although visual cues are used in the present embodiment, the present invention is well suited to the use of other cues such as for example audible cues. Such audible cues may include, for example, beeps or other sounds which are emitted from display unit 32 of FIG. 2 when image 50 differs from image 60. Additionally, the present invention changes the intensity or pitch of the beeps to indicate large or small variations in the position of image 50 from the position of image 60.

Figure 8A:
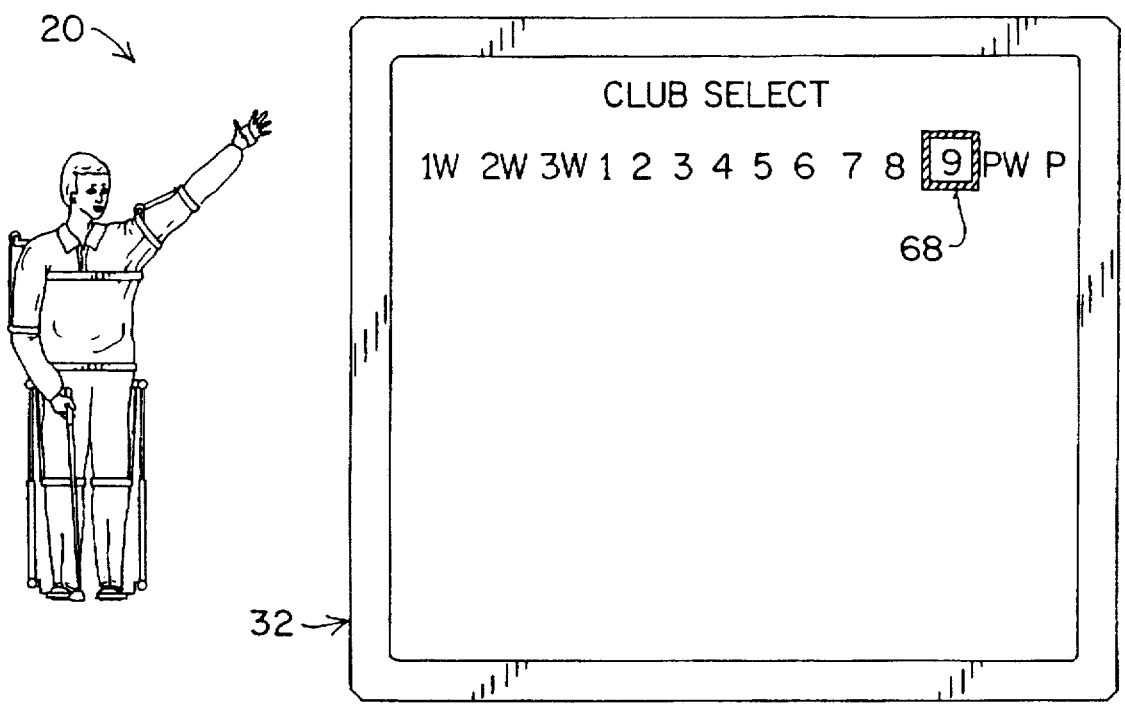
FIGS. 8A and 8B show another embodiment of the present claimed invention in which the motion measurement apparatus of the present invention is utilized by the user in conjunction with a display as a "keyboard" or "mouse" in accordance with the present claimed invention.
Figure 8B:
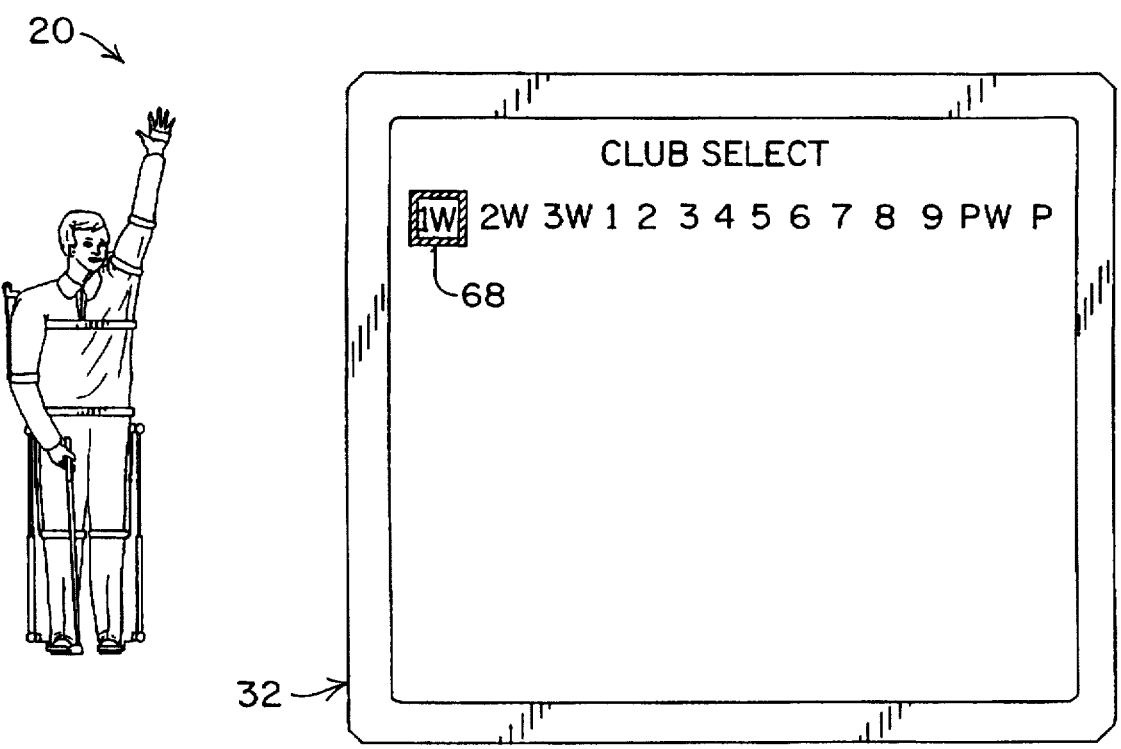

With reference next to FIGS. 8A and 8B, another embodiment is shown in which the motion measurement apparatus of the present invention is used by golfer 20 as a "keyboard" or "mouse" in conjunction with display unit 32. Although used by a golfer in the present embodiment, the present invention is also well suited for use in other areas such as, for example, as a head tracking apparatus in virtual reality application. Additionally, by attaching motion sensors to the head of a user using, for example, a headband, the present invention could also be employed as a "head mouse" for use by, for example, computer user. In such instances, calibration means and rate control means are used to refine and translate motions of the head of a computer user to movement of, for example, a cursor or pointer on a computer screen.

With reference now to FIG. 8A in the present embodiment, when golfer 20 raises only his left arm above his head, a predetermined function is invoked and the present invention places a specific message on display 32. In the present embodiment, the "Club Select" function is displayed on display unit 32 when golfer 20 raises only his left arm above his head. As shown on display unit 32 of FIG. 8A, the Club Select function allows golfer 20 to indicate which club golfer 20 will be swinging by moving the position of window 68 over the desired club. In the present embodiment, golfer 20 may select from clubs ranging from the 1 wood (1W) to the putter (P). Although such a selection of clubs is available to golfer 20 in the present embodiment, the present invention is also well suited to numerous variations on the number or types of clubs which may be selected.

With reference still to FIGS. 8A and 8B, in the present embodiment, golfer 20 moves the position of window 68 by moving his extended left arm nearer to or farther from his head. As shown in FIG. 8A, as golfer 20 moves his extended left arm away from his head, window 68 moves to the right or towards the putter (P) on display unit 32. As shown in FIG. 8B, when golfer 20 moves his extended left arm nearer his head, window 68 moves to the left or towards the one wood (1W) on display unit 32. Although such movements and a Club Select function are set forth in the present embodiment, the present invention is also well suited to the use of numerous other types of functions which are selected and controlled using various other body positions and body movements.

Figure 9:
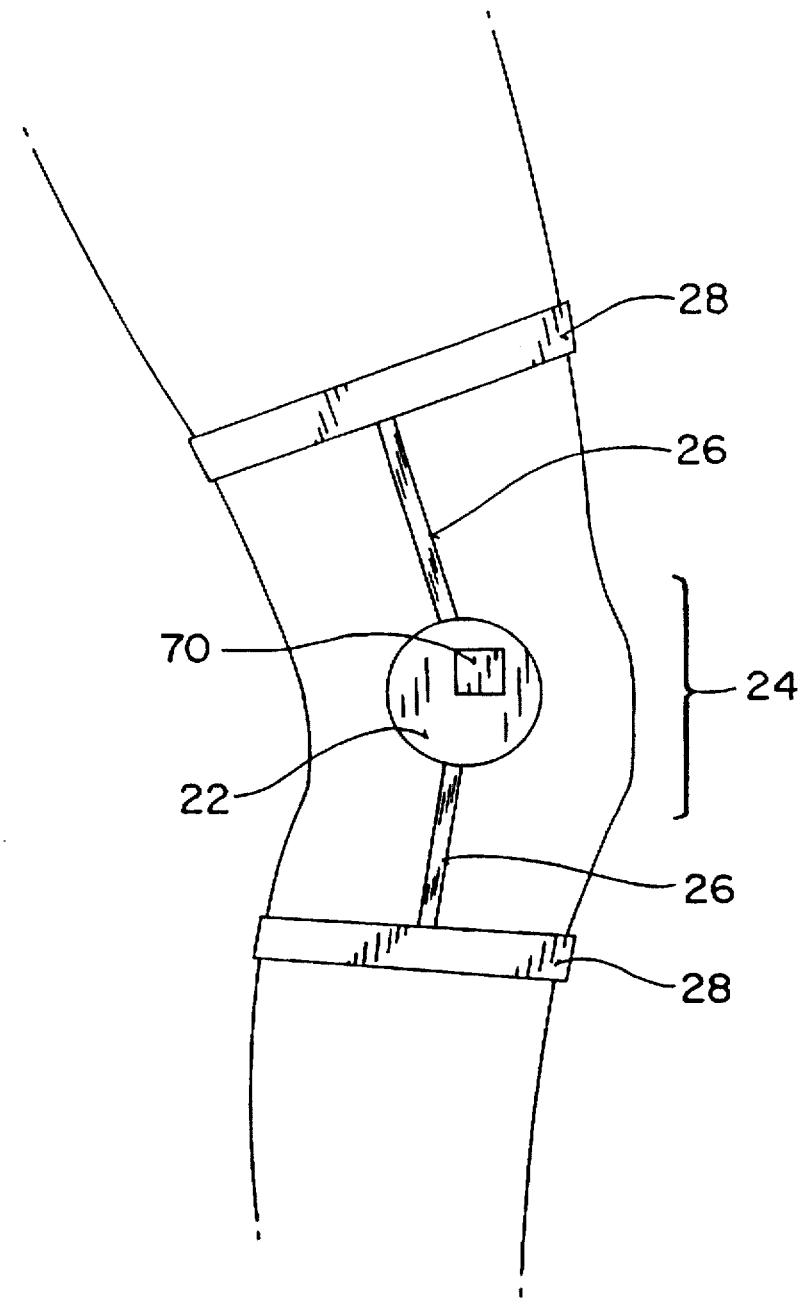
FIG. 9 is a side view of a knee joint in another embodiment of the present claimed invention in which a small vibrating mechanism is attached to a sensor located on the knee joint of a golfer in accordance with the present claimed invention.

With reference next to FIG. 9, another embodiment of the present invention is shown in which a small vibrating mechanism 70 is attached to sensor 22 located on the knee joint 24 of golfer 20 of FIG. 2. Vibrator 70 is electrically coupled to processor 30 of FIG. 2. If images 50 of FIGS. 6A, 6B, and 7, differs from image 60, vibrators 70 on sensors 22 will vibrate those joints of golfer 20 which are improperly positioned. In so doing, golfer 20 is directly alerted as to which joints must be adjusted in order for image 50 to match image 60. Thus, golfer 20 is able to receive direct stimulation of his body only at those locations which are improperly positioned. In addition the present invention is also well suited to the attachment of a plurality of vibrating mechanisms to the body of golfer 20. For example, one vibrating mechanism may be placed at the front of knee joint 24, and a second vibrating mechanism may be located at the back of knee joint 24. If the knee of golfer 24 is bent too far, the vibrating mechanism on the front of the knee joint will be activated thereby instructing golfer 20 to straighten his knee. Likewise, if the knee of golfer 20 is too straight, the vibrating mechanism on the back of knee joint 24 will be activated thereby instructing golfer 20 to bend his knee. Although the use of multiple vibrating mechanisms is described in the present embodiment in conjunction with knee joint 24, multiple vibrating mechanisms may be employed in various combinations at numerous joints of golfer 20. Furthermore, although a vibrating mechanism is set forth in the present embodiment, the present invention is also well suited to the use of other tactile stimuli such as, for example, a mild electric shocking mechanism.

Figure 10A:
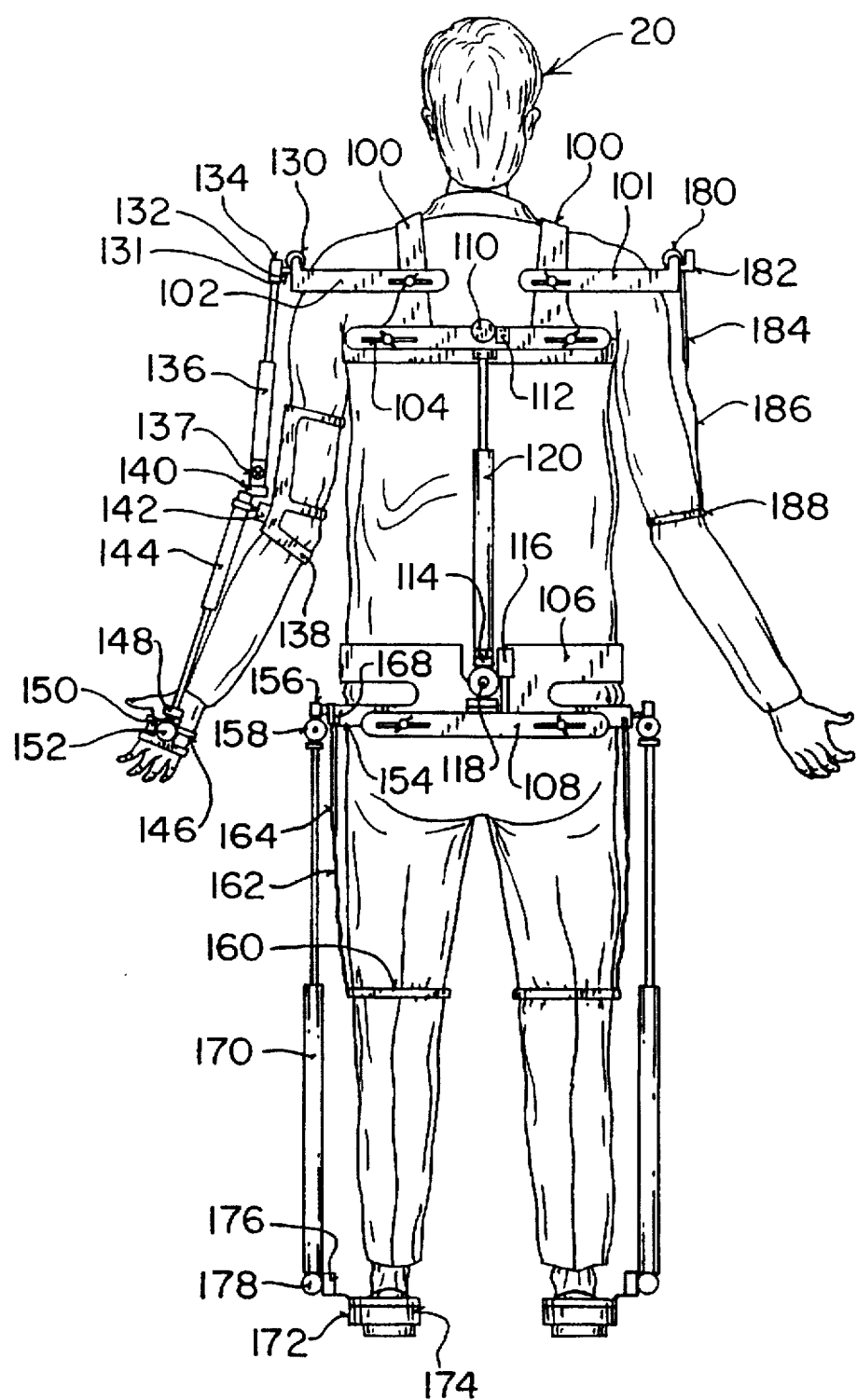
FIGS. 10A–H are views of the structure of one embodiment of a motion measurement apparatus in accordance with the present claimed invention.

With reference next to FIGS. 10A–10H, another embodiment of the present invention is set forth in which the structure of a motion measurement apparatus of the present invention is set forth in detail. FIG. 10A is a rear view of a right handed golfer 20, having the present invention attached to his body. As shown in FIG. 10A, a harness fits over the shoulders of golfer 20. Adjustable right and left shoulder brackets 101, 102 are attached to harness 100 using, for example, wing nuts, not shown, such that the position of right and left shoulder brackets 101, 102 may be adjusted to accommodate various shoulder widths. An upper back bracket 104 is also attached to harness 100 using, for example, wing nuts, not shown, such that the position of upper back bracket 104 may be adjusted to accommodate back sizes. A hip harness 106 is attached around the waist area of golfer. A lower back bracket 108 is attached to hip harness 106 using, for example, wing nuts, not shown, such that the position of lower back bracket 108 may be adjusted to accommodate various lower back sizes. Various potentiometers 110, 112 are coupled to upper back bracket 104. Likewise, various potentiometers 114, 116, and 118 are disposed on lower back bracket 108. A telescopic sliding torque transmitting lever connector 120 couples upper back bracket 104 and lower back bracket 108.

Figure 10B:
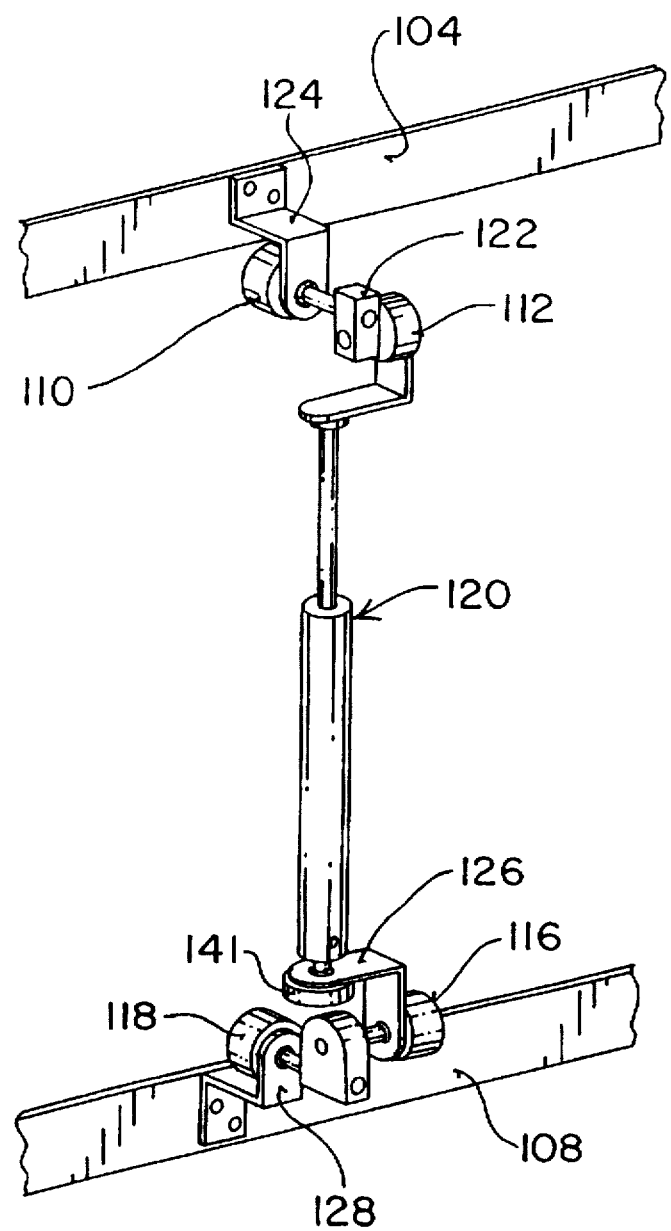

With reference next to FIG. 10B a detailed perspective view of potentiometers 110, 112, potentiometers 114, 116, and 118, and telescopic sliding torque transmitting lever connector 120 are shown in detail. As shown in FIG. 10B, potentiometers 110, 112, are coupled to upper back bracket 104 using, for example, clamps 122 and 124. All of the potentiometers of the present embodiment function in a similar manner. That is, as the potentiometer is rotated about its axis, the resistance within the potentiometer is altered. As a result, the outgoing voltage varies according to the amount of rotation to which the potentiometer is subjected. Thus, a precise measurement of the amount of rotation occurring at each potentiometer, and a corresponding portion of the body of golfer 20 of FIG. 10A can be obtained. Wires, not shown, electrically connect each of the potentiometers to a processor such as, for example, processor 30 of FIG. 2.

With reference still to FIG. 10B, potentiometer 110 measures the horizontal movement of the shoulders of golfer 20 of FIG. 10A with respect to the spine of golfer 20. Potentiometer 112 is attached to clamp 122 such that potentiometer 112 measures the front-to-back movement of the shoulders of golfer 20 with respect to the spine of golfer 20. Telescopic sliding torque transmitting lever connector 120 delivers torque to potentiometer 114 such that the rotation of the spine of golfer 20 is quantitatively measured. Potentiometer 116 is attached to clamp 126 such that potentiometer 116 measures the front-to-back tilt of the spine of golfer 20 with respect to the hips of golfer 20. Finally, potentiometer 118 is attached to clamp 128 in order to measure changes in the position of the hips of golfer 20 with respect to the spine of golfer 20. Specifically, potentiometer 118 measures variations from the substantially perpendicular alignment of the spine of golfer 20 to the hips of golfer 20.

With reference again to FIG. 10A, the left arm of golfer 20 also has a plurality of potentiometers 130, 131, 134, 140, 142, 148, 150, 152, clamp 132, bracket 102, harnesses 138, 146, and telescopic sliding torque transmitting lever connectors 136, 144, attached thereto.

Figure 10C:
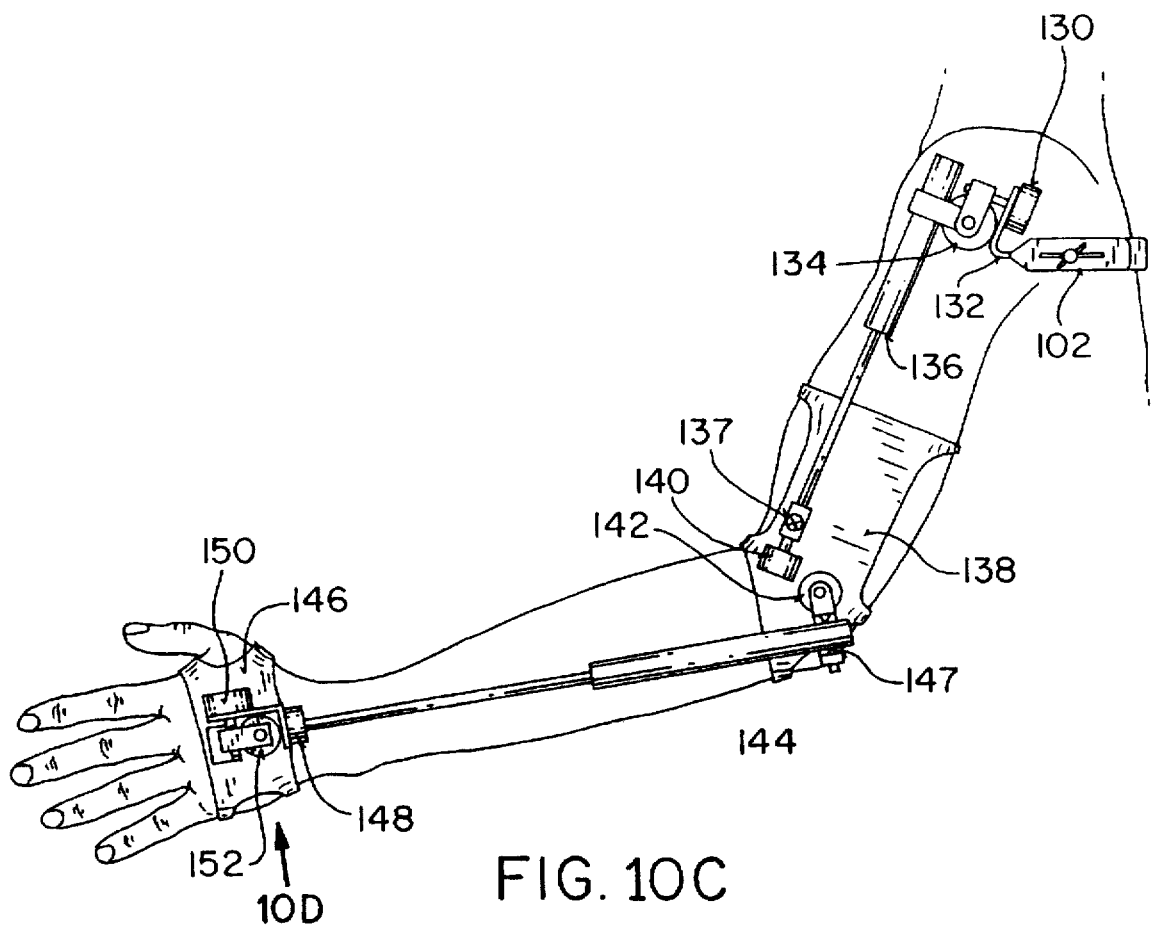

With reference next to FIG. 10C, a detailed description of the arrangement of potentiometers 130, 131, 134, 140, 142, 148, 150, 152, clamp 132, bracket 102, harnesses 138, 146, and telescopic sliding torque transmitting lever connectors 136, 144, attached to the left arm of golfer 20 of FIG. 10A thereto is set forth. A potentiometer 130 is attached to clamp 132 connected to left shoulder bracket 102. Potentiometer 130 measures movement of the upper portion of the left arm of golfer 20 away from or towards the body of golfer 20. Also attached to potentiometer 130 is a potentiometer 134 for measuring the front-to-back motion of the left arm of golfer 20. Potentiometer 131 measures rotational movement of the upper left arm of golfer 20. A telescopic sliding torque transmitting lever connector 136, is attached to potentiometer 134.

With reference still to FIG. 10C, an elbow harness 138 has a potentiometer 140 attached thereto and coupled to telescopic sliding torque transmitting lever connector 136 via a universal type joint configuration 137 in order to measure the rotation of the left upper arm of golfer 20. Additionally, elbow harness 138 has a potentiometer 142 attached thereto in order to measure the extension or bending occurring at the left elbow of golfer 20. Furthermore, one end of a telescopic sliding torque transmitting lever connector 144 is coupled to potentiometer 142 using joint 147. A wrist harness 146 is attached to the left wrist of golfer 20 and has the second end of telescopic sliding torque transmitting lever connector 144 connected to a potentiometer 148 attached thereto. Potentiometer 148 measures the rotation of the left wrist of golfer 20 with respect to the left elbow of golfer 20, and is coupled to potentiometer 150 which measures whether the wrist of the left hand of golfer 20 is held straight out from the lower arm or is bent up or down with respect to the lower arm of golfer 20. Finally, potentiometer, 152 coupled to potentiometer 150 and wrist harness 146 measures whether the wrist of golfer 20 is held straight out, is bent inward such that the thumb on the left hand approaches the inside of the lower left arm, or whether the wrist is bent outward such that the small finger of the hand is bent towards the outside of the lower left arm of golfer 20.

Figure 10D:
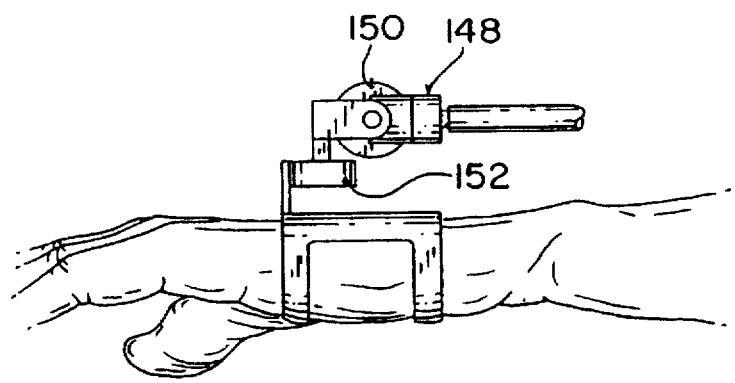

With reference next to FIG. 10D, a view of the present invention taken along line D of FIG. 10C is shown.

Figures 10E, 10F:
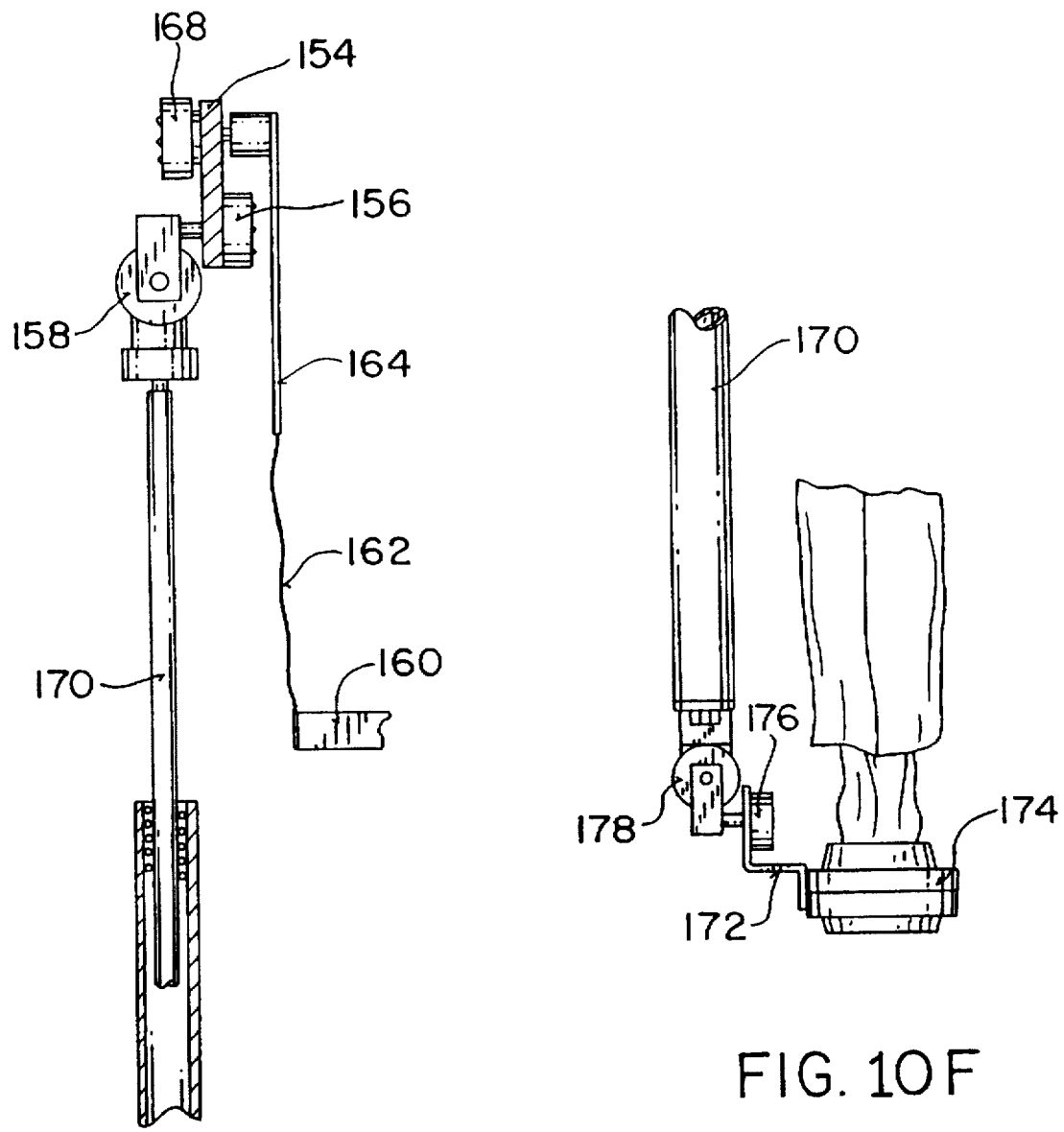

With reference next to FIG. 10E a partial view of the present invention attached to the left leg of golfer 20 of FIG. 10A is shown. A left thigh clamp 154 is attached to lower back bracket 108. A potentiometer 156 measures the front-to-back motion of the left leg of golfer 20. Another potentiometer 158 measures the extent to which the left leg of golfer 20 is extended to the side away from the left side of golfer 20.

With reference again to FIG. 10E, a strap 160 is placed around the left knee of golfer 20. An elastic connector 162 extends from strap 160 to a lever arm 164. Lever arm 164 is coupled to a potentiometer 168 which measures the motion of the left knee of golfer 20. As shown in FIG. 10E, a telescopic sliding torque transmitting lever connector 170 extends downwardly from the outside of the left hip of golfer 20 towards the outside of the left ankle of golfer 20.

With reference next to FIG. 10F, a bracket 172 is attached to a left foot harness 174 worn on the left foot of golfer 20. Attached to bracket 172 is a potentiometer 176 for measuring whether the heel or toes of golfer 20 are pulled upward. Another potentiometer 178 measures the side to side motion of the foot of golfer 20. The motion of the right leg of golfer 20 is measured using a similar structure. Additionally, although not shown in the present embodiment, the present invention is well suited to having bracket 172 coupled directly to the ground, such that the ground can be used as a reference point for the positioning of golfer 20. Furthermore, although not shown, the present invention is also well suited to using means such as, for example, a gyroscope, a radio receiver, an optical system, or a magnetic link to provide a quantitative measurement of the position of golfer 20 with respect to the ground and even with respect to a golf ball or golf club.

Figure 10G:
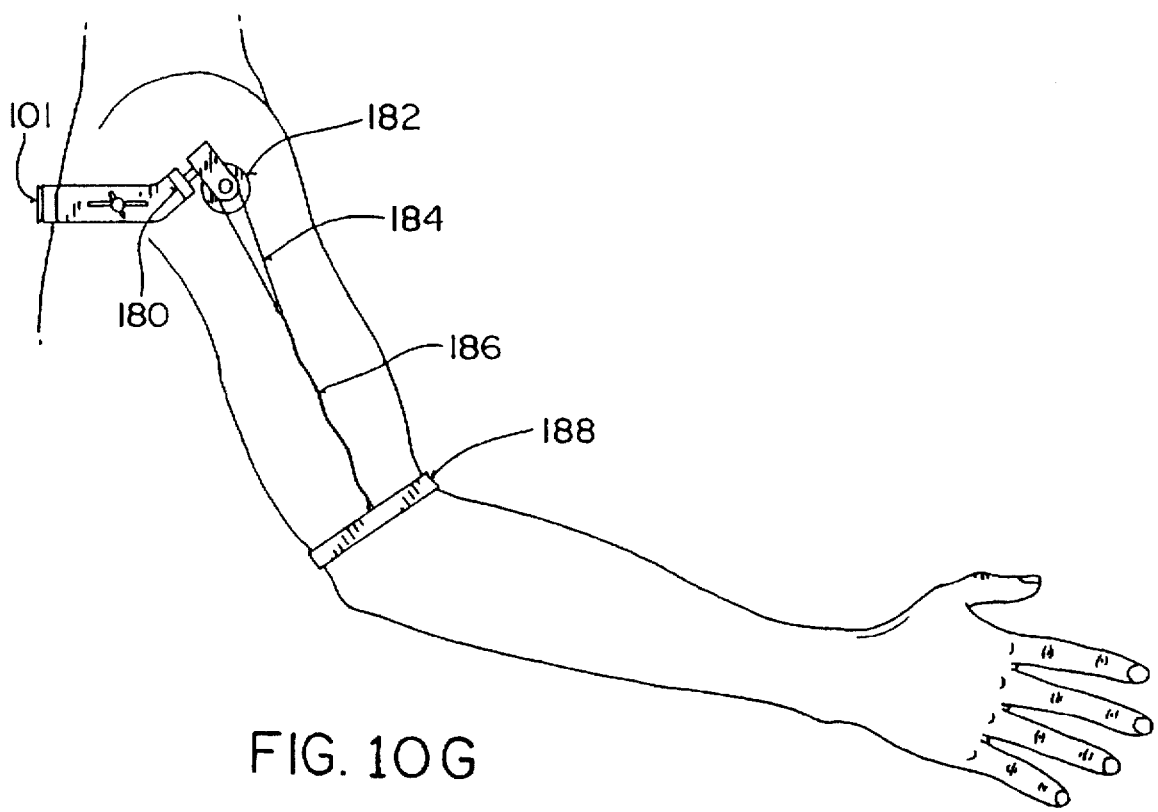

With reference next to FIG. 10G, the attachment of the present invention to the right shoulder of golfer 20 is shown in detail. A potentiometer 180 is coupled to right shoulder bracket 101. Potentiometer 180 measures movement of the upper portion of the right arm of golfer 20 away from or towards the body of golfer 20. A second potentiometer 134 measures the front-to-back motion of the right arm of golfer 20 using a lever arm 184 having an elastic band 186 attached to elbow strap 188.

Figure 10H:
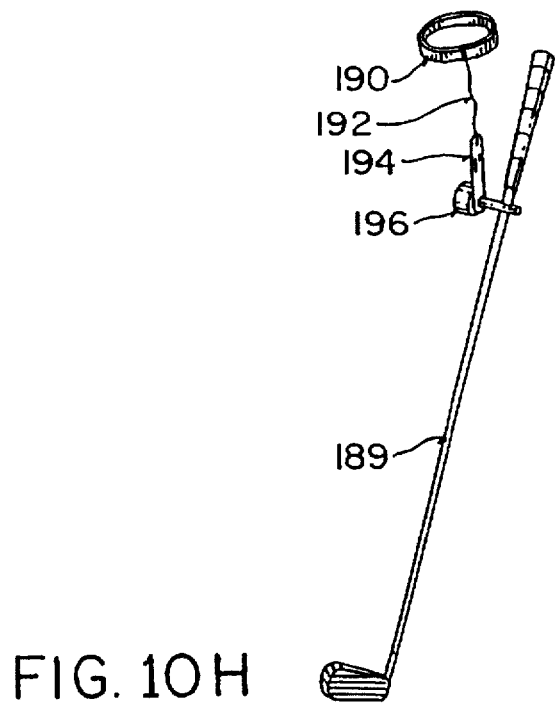

With reference next to FIG. 10H, the positioning and movement of the right hand of golfer 20 on a golf club 189 is measured using a right wrist strap 190, and elastic band 192, a lever arm 194, and a potentiometer 196. Wrist strap 190 is connected using elastic band 192 to lever arm 194. Lever arm 194 is coupled to potentiometer 196 attached to golf club 189. In so doing, the movement of the right hand of golfer 20 with respect to golf club 189 is quantitatively measured.

Figure 11A:
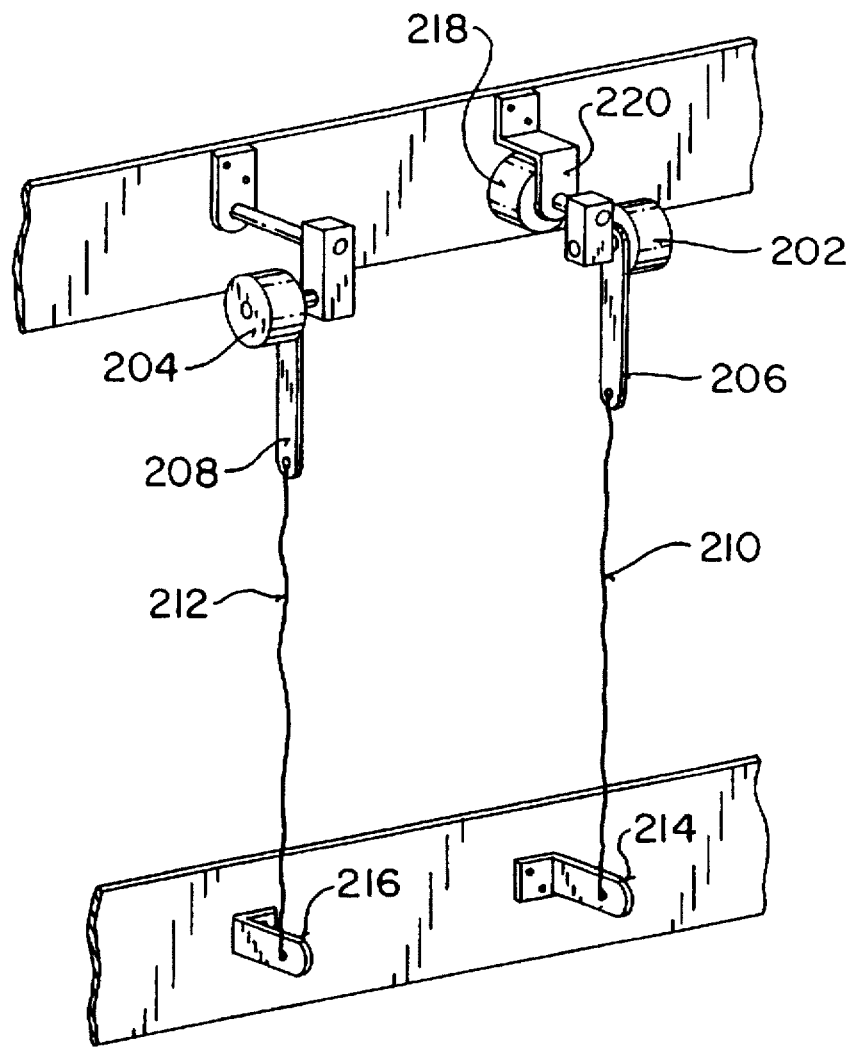
FIG. 11A is a perspective view of an alternate arrangement of a motion measurement apparatus in accordance with the present claimed invention.

With reference next to FIG. 11A, an alternate embodiment of the present invention is shown in which an alternate arrangement of potentiometers and lever arms is used to measure the movement of a joint of golfer 20. As shown in FIG. 11, sensors such as, for example, potentiometers 202 and 204 are attached to lever arms 206 and 208 respectively. Lever arms 206 and 208 are then respectively connected to elastic bands 210 and 212 which in turn are connected to brackets 214 and 216 respectively. Potentiometer 200 is also coupled to potentiometer 218 via bracket 220. Assuming that the alternate arrangement of FIG. 11 is attached to the back of golfer 20, then potentiometer 218 measures side to side motion of golfer 20, while potentiometers 202 and 204 measure front to back motion of golfer 20. Rotation of the back of golfer 20 is determined by the difference between the amount of rotation recorded at potentiometers 202 and 204. For example, if potentiometer 202 measures rotation, $\theta_{202}$, and potentiometer 204 measures rotation, $\theta_{204}$, then the rotation of the back of golfer 20, $\theta_{back}$, is given by $\theta_{202} - \theta_{204}$.

Figure 11B:
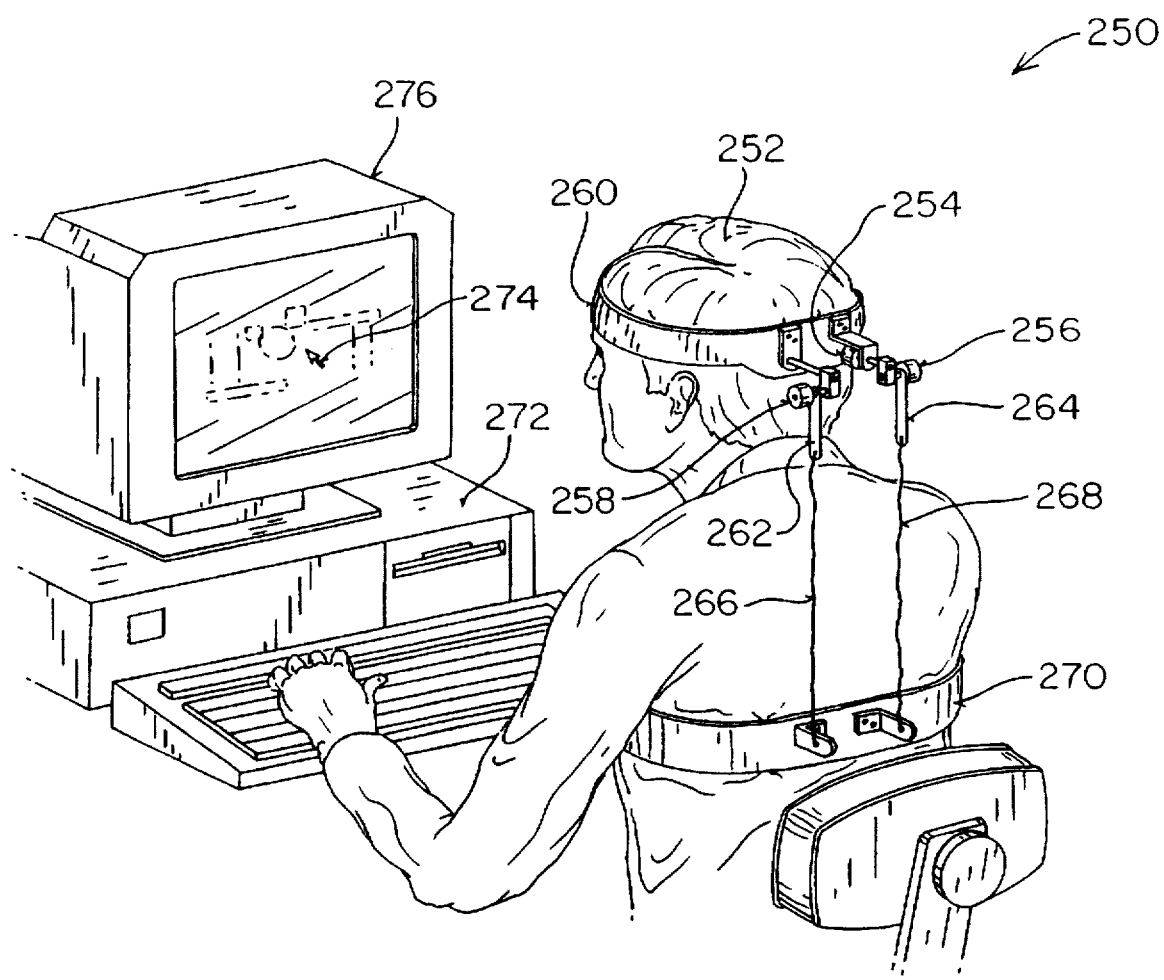
FIG. 11B is a perspective view of an alternate embodiment of a motion measurement apparatus wherein the apparatus is used as a head mouse in accordance with the present claimed invention.

With reference next to FIG. 11B, an application of the alternate embodiment of FIG. 11A is shown. Specifically, as described above in the discussion of FIGS. 8A and 8B, a head mouse 250 is shown attached to the head of a computer user 252. As shown in FIG. 11B, motion sensors 254, 256, and 258 are coupled to a headband 260 worn by the computer user. Motion sensors 254, 256, and 258 are coupled using lever arms 262 and 264, and elastic bands 266 and 268 to for example a strap 270 worn on the back of computer user 252. Head mouse 250 is electrically coupled to a computer 272, such that motion of the head of computer user 252 translates into motion of a cursor or pointer 274 on a computer screen 276. A "mouse button", not shown, is mounted for example on a computer keyboard also not shown, for performing task associated with conventional mouses such as highlighting, dragging, and selecting, for example. In addition, head mouse 250 includes calibration means for initially placing cursor 274 in a desired position on computer screen 276. Rate control means, not shown, are also provided to appropriately relate head movement of user 252 to movement of cursor 274. Although sensors 254, 256, and 258 are coupled to headband 260 in the present embodiment, the present invention is also well suited to alternate configurations including having sensors coupled, for example to the back of the chair in which the user is sitting. Additionally, the present invention is well suited to having at least one sensor positioned to measure "nodding" motions by the user. Furthermore, the present invention is also well suited to head motion measurement configurations including but not limited to using two sensors and two levers, using two sensors and one lever.

Figure 12:
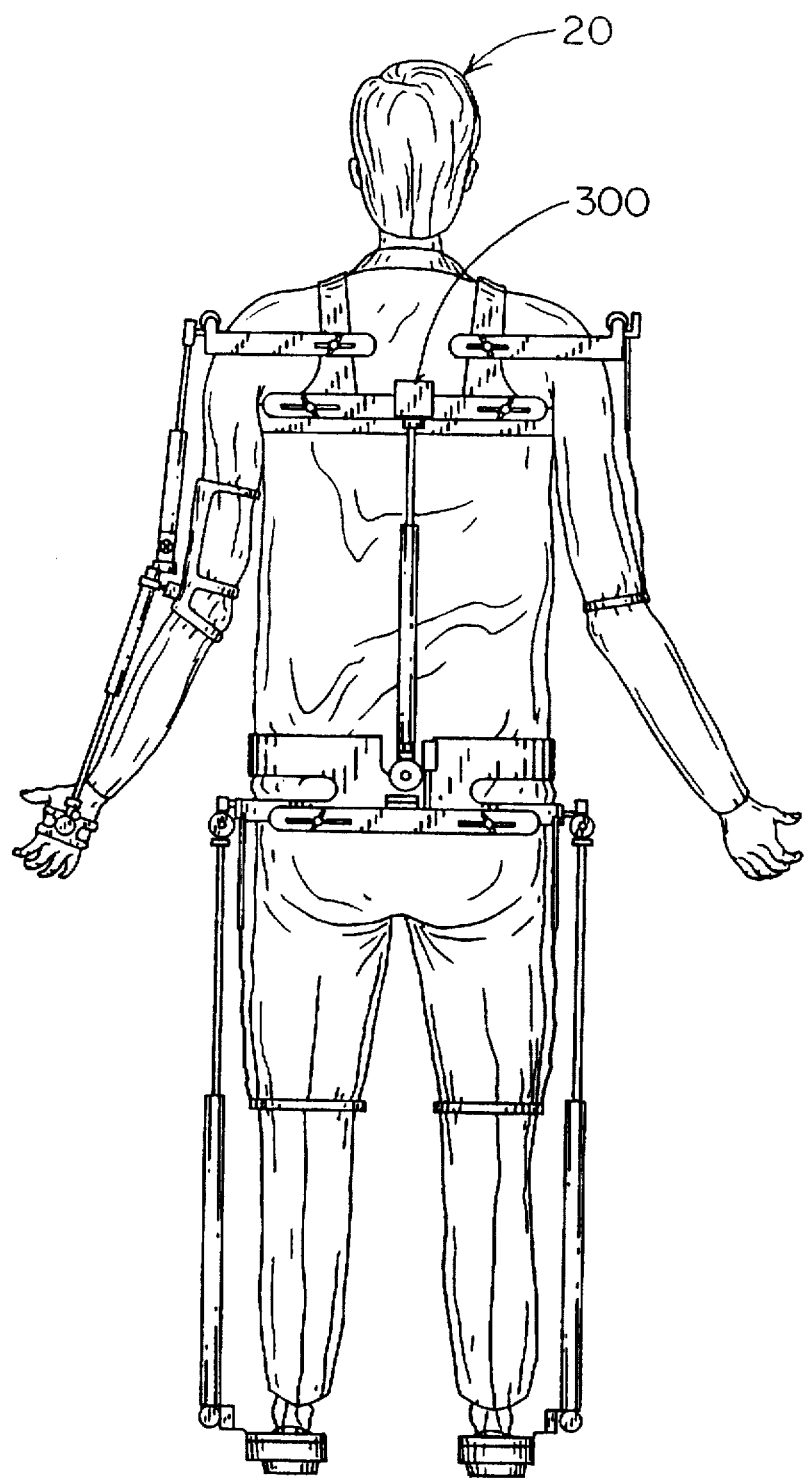
FIG. 12 is a perspective view of an alternate embodiment of a motion measurement apparatus wherein the apparatus included gyroscope means in accordance with the present claimed invention.

With reference next to FIG. 12, an alternate embodiment of the present invention is shown. Specifically, as described above in the discussion of FIG. 10F, a motion measurement apparatus employing gyroscopic magnetometer or other self-referencing means 300 is shown. Self-referencing means 300 are placed for example in the upper back region of golfer 20. In so doing, self-referencing means 300 is able to provide output to processor means, not shown, in order to provide a quantitative measurement of the position of golfer 20 with respect to the ground and even with respect to a golf ball or golf club.

Thus, the present invention provides a compact, inexpensive system to monitor the movement of a human body while performing a motion such as, for example, a golf swing, which does not require the complex detection systems found in the prior art, and which provides for approximate real time observation of the body movement of a golfer while performing the golf swing. Additionally, the compact size of the present invention provides for portability which was not found in the prior art, thereby allowing the golfer to use the present invention wherever he desires.

I claim:

1. An apparatus for measuring body limb movement comprising:
    a) a torque transmitting lever having a first end and a second end and a longitudinal axis extending from said first end to said second end,
    b) a rotation sensor,
    c) a first body joint attachment means,
    d) a second body joint attachment means,
    e) said first body joint attachment means connected to said first end of said torque transmitting lever,
    f) said second body joint attachment means connected to said rotation sensor,
    g) said rotation sensor connected to said second end of said torque transmitting lever for sensing rotation of said torque transmitting lever about said longitudinal axis, whereby the rotation of a limb around its longitudinal axis is measured.

2. The limb movement measurement apparatus of claim 1 further comprising at least one universal joint coupled to at least one end of said lever.

3. The limb movement measurement apparatus of claim 1 wherein said torque transmitting lever is slidably extensible.

4. The limb movement measurement apparatus of claim 3 wherein said torque transmitting lever is a telescopic sliding rod having means for transmitting torque about said longitudinal axis from said first end to said second end.

5. The limb movement measurement apparatus of claim 3 wherein said rotation sensor is of the variable resistance type.

6. The limb movement measurement apparatus of claim 3 wherein said rotation sensor is a potentiometer.

7. An apparatus for measuring body limb movement comprising:
   a) a slidably extensible torque transmitting lever,
   b) a first rotation sensor,
   c) a first body joint attachment means,
   d) a second body joint attachment means,
   e) said first body joint attachment means connected to a first end of said torque transmitting lever,
   f) said second body joint attachment means connected to said first rotation sensor,
   g) said first rotation sensor connected to a second end of said torque transmitting lever,
   h) a second rotation sensor,
   i) means for attaching said second rotation sensor to said first body joint attachment means,
   j) means for attaching said second rotation sensor to said first end of said lever,
whereby at least one angle of movement of at least one limb joint and rotation of the limb are measured simultaneously.

8. An apparatus for measuring body limb movement comprising:
   a) a slidably extensible torque transmitting lever,
   b) a first rotation sensor,
   c) a first body joint attachment means,
   d) a second body joint attachment means,
   e) said first body joint attachment means connected to a first end of said torque transmitting lever,
   f) said second body joint attachment means connected to said first rotation sensor,
   g) said first rotation sensor connected to a second end of said torque transmitting lever,
   h) a second rotation sensor,
   i) means for attaching said second rotation sensor to said first body joint attachment means,
   j) means for coupling said second rotation sensor to said first rotation sensor,
whereby at least one angle of movement of at least one limb joint at an end of the limb and rotation of the limb are measured simultaneously.

9. The limb movement measurement apparatus of claim 7 wherein said torque transmitting lever is a telescopic sliding rod having means for transmitting torque about said longitudinal axis from said first end to said second end.

10. The limb movement measurement apparatus of claim 8 wherein said torque transmitting lever is a telescopic sliding rod having means for transmitting torque about said longitudinal axis from said first end to said second end.

11. The limb movement measurement apparatus of claim 8 wherein one said joint attachment means is a wrist attachment means and the other said joint attachment means is an elbow attachment means, whereby the angles of the wrist joint and the rotation of the lower arm and angle of elbow joint are measured.

12. The limb movement measurement apparatus of claim 8 wherein one said joint attachment means is an elbow attachment means and the other said joint attachment means is a shoulder attachment means, whereby the angle of the elbow joint and the rotation of the upper arm and angle of the shoulder joint are measured.

13. The limb movement measurement apparatus of claim 8 wherein one said joint attachment means is an ankle attachment means and the other joint attachment means is a knee attachment means, whereby the angles of the ankle and the rotation of the lower leg and the angle of the knee is measured.

14. The limb movement measurement apparatus of claim 8 wherein one said joint attachment means is a knee attachment means and the other said joint attachment means is a hip attachment means, whereby the angles of the hip and the rotation of the upper leg are measured.

15. An apparatus for measuring upper body motion comprising:
   a) a slidably extensible torque transmitting lever,
   b) hip attachment means,
   c) shoulder attachment means,
   d) plurality of rotation sensors,
   e) means for coupling said rotation sensors to ends of said lever,
   f) means for coupling said rotation sensors to said hip and shoulder attachment means,
whereby said rotation sensors simultaneously sense the rotation and bending of spine and the movements of the hips and the shoulders.

16. The limb movement measurement apparatus of claim 15 wherein said torque transmitting lever is a telescopic sliding rod having means for transmitting torque about said longitudinal axis from said first end to said second end.

17. A method of measuring body movement comprising:
   a) attaching a first end of a torque transmitting lever to a first point on a user's body;
   b) connecting a first rotation sensor to a second end of the torque transmitting lever;
   c) attaching the first rotation sensor to a second point on the user's body;
   d) measuring relative rotation between the first point on the user's body and the second point on the user's body by sensing rotation of the torque transmitting lever about a longitudinal axis extending from the first end to the second end of the torque transmitting lever.

18. The method as recited in claim 17 further comprising the step of processing signals from the rotation sensor indicative of the relative rotation between the first point on the user's body and the second point on the user's body.

19. The method as recited in claim 18 further comprising the step of visually displaying at least one image representing movement of the user's body.

20. The method of claim 17 further comprising slidably extending the torque transmitting lever.

21. The method of claim 17 further comprising telescopically extending the torque transmitting lever and transmitting torque about said longitudinal axis from the first end to the second end of the torque transmitting lever.

22. The method of claim 17 further comprising:
   e) connecting a second rotation sensor to the first end of the torque transmitting lever;
   f) measuring angular movement between the first point on the user's body and the second point on the user's body by sensing rotation of the torque transmitting lever about a second axis.

23. The method of claim 17 further comprising:
   e) coupling a second rotation sensor to the rotation sensor;
   f) measuring angular movement between the first point on the user's body and the second point on the user's body by sensing rotation of the torque transmitting lever about a second axis.

* * * * *